United States Patent
Chung

(10) Patent No.: US 12,414,996 B2
(45) Date of Patent: Sep. 16, 2025

(54) ORGANIC ANION TRANSPORTING PEPTIDE-BASED CANCER IMAGING AND THERAPY

(71) Applicant: Da Zen Theranostics, Inc., Beverly Hills, CA (US)

(72) Inventor: Leland W. K. Chung, Beverly Hills, CA (US)

(73) Assignee: Da Zen Theranostics, Inc., Beverly Hills, CA (US)

( * ) Notice: Subject to any disclaimer, the term of this patent is extended or adjusted under 35 U.S.C. 154(b) by 1106 days.

(21) Appl. No.: 17/318,802

(22) Filed: May 12, 2021

(65) Prior Publication Data

US 2022/0031855 A1     Feb. 3, 2022

Related U.S. Application Data

(63) Continuation of application No. 16/390,384, filed on Apr. 22, 2019, now abandoned, which is a continuation of application No. 15/538,359, filed as application No. PCT/US2015/067393 on Dec. 22, 2015, now Pat. No. 10,307,489.

(60) Provisional application No. 62/095,713, filed on Dec. 22, 2014.

(51) Int. Cl.

| | |
|---|---|
| *A61B 5/00* | (2006.01) |
| *A61B 8/00* | (2006.01) |
| *A61B 10/00* | (2006.01) |
| *A61K 47/54* | (2017.01) |
| *A61K 51/04* | (2006.01) |
| *G01N 33/574* | (2006.01) |
| *A61K 49/00* | (2006.01) |

(52) U.S. Cl.
CPC ........ *A61K 47/558* (2017.08); *A61K 51/0446* (2013.01); *G01N 33/57407* (2013.01); *A61K 49/0017* (2013.01)

(58) Field of Classification Search
CPC .............. A61K 47/558; A61K 51/0446; A61K 49/0017; G01N 33/57407; C09B 23/0066; A61P 35/00
See application file for complete search history.

(56) References Cited

U.S. PATENT DOCUMENTS

| | | | |
|---|---|---|---|
| 9,771,625 B2* | 9/2017 | Shih ................... | A61K 47/6929 |
| 10,307,489 B2* | 6/2019 | Chung ................. | A61P 35/00 |
| 2013/0101513 A1* | 4/2013 | Yang ..................... | C12Q 1/04 |
| | | | 424/9.1 |
| 2014/0248213 A1* | 9/2014 | Chung ................. | A61B 5/0075 |
| | | | 540/472 |

* cited by examiner

*Primary Examiner* — Michael G. Hartley
*Assistant Examiner* — Melissa J Perreira
(74) *Attorney, Agent, or Firm* — Fox Rothschild LLP

(57) ABSTRACT

A dye-drug conjugate for preventing, treating, or imaging cancer having the following structure:

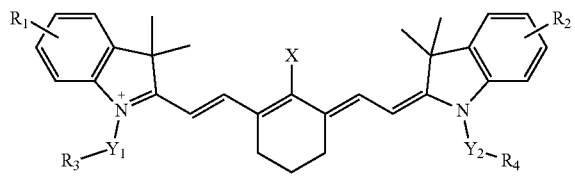

wherein $R_1$ and $R_2$ are independently selected from the group consisting of —H, alkyl, alkyl-sulphonate, alkylcarboxylic, alkylamino, aryl, —$SO_3H$, —$PO_3H$, —OH, —$NH_2$, and -halogen; wherein $Y_1$ and $Y_2$ is independently selected from the group consisting of alkyl, aryl, aralkyl, alkylsulphonate, alkylcarboxylic, alkylamino, ω-alkylaminium, ω-alkynyl, PEGyl, PEGylcarboxylate, ω-PEGylaminium, ω-acyl-NH, ω-acyl-lysinyl-, ω-acyl-triazole, ω-PEGylcarboxyl-NH—, ω-PEGylcarboxyl-lysinyl, and ω-PEGylcarboxyl-triazole; wherein X is selected from the group consisting of a hydrogen, halogen, CN, Me, $NH_2$, SH and OH; and $R_3$ and $R_4$ are independently a hydrogen, a therapeutic agent, or an imaging moiety, wherein the therapeutic agent is selected from the group consisting of a platinum-based therapeutic agent, a small molecule therapeutic agent, a peptide, a protein, a polymer, an siRNA, a microRNA, and a nanoparticle, wherein the imaging is a radio-isotope selected from the group consisting of F18, I-125, I-124 I-123, I-131, and small molecule labeled with any of these isotopes, or wherein the imaging moiety is a chelator-complexed radioactive isotope, wherein the radioactive isotope is selected from the group consisting of Cu-64, In-111, Tc-99m, Ga-68, Lu-177, Zo-89, Th-227 and Gd-157.

18 Claims, 15 Drawing Sheets

DZ-1

FIG 1(C)
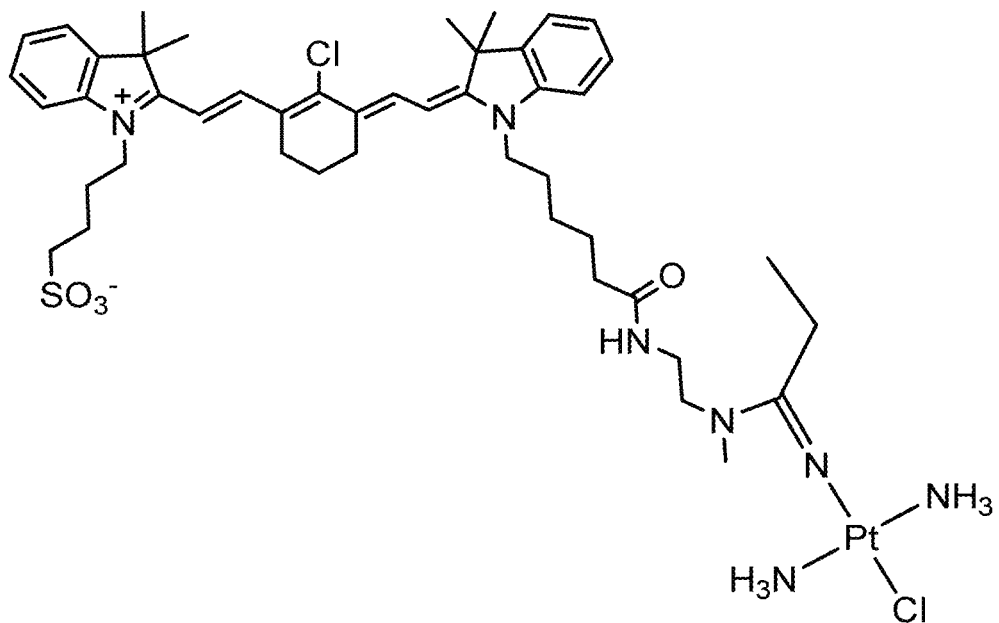
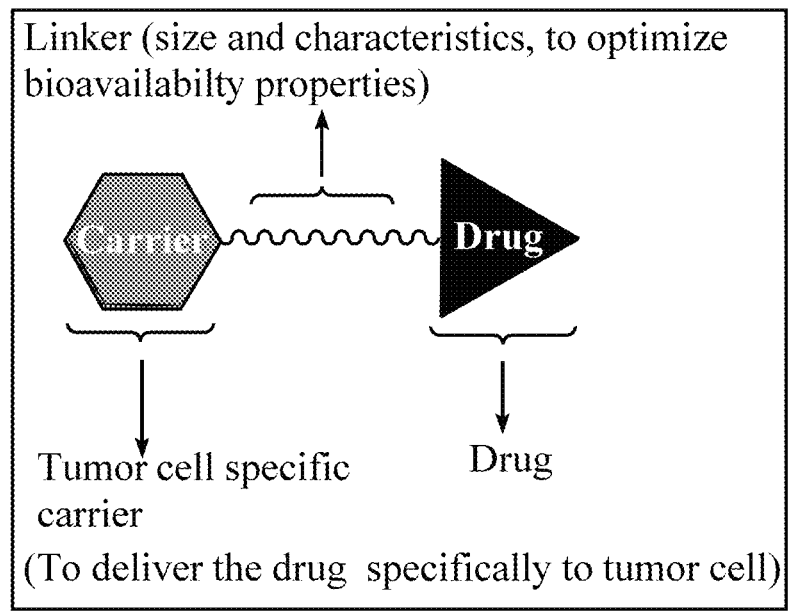
FIG. 2. Conceptual design of drug-carrier conjugate

ORGANIC ANION TRANSPORTING PEPTIDE-BASED CANCER IMAGING AND THERAPY

CROSS-REFERENCE TO RELATED APPLICATIONS

The present application is a continuation of U.S. patent application Ser. No. 16/390,384, filed 2019 Apr. 22, which is a continuation of U.S. patent application Ser. No. 15/538,359, filed Jun. 21, 2017, which is a national stage application of, and claims the benefit to, PCT Application No. PCT/US2015/067393 filed Dec. 22, 2015, which claims priority to U.S. Patent Application Ser. No. 62/095,713, filed Dec. 22, 2014, the entire disclosures of which are incorporated herein by reference.

TECHNICAL FIELD OF THE INVENTION

A dye-drug conjugate for preventing, treating, or imaging cancer having the following structure:

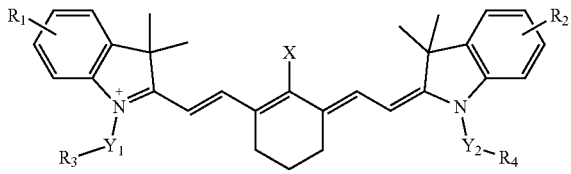

wherein $R_1$ and $R_2$ are independently selected from the group consisting of —H, alkyl, alkyl-sulphonate, alkylcarboxylic, alkylamino, aryl, —$SO_3H$, —$PO_3H$, —OH, —$NH_2$, and -halogen; wherein $Y_1$ and $Y_2$ is independently selected from the group consisting of alkyl, aryl, aralkyl, alkylsulphonate, alkylcarboxylic, alkylamino, ω-alkylaminium, ω-alkynyl, PEGyl, PEGylcarboxylate, ω-PEGylaminium, ω-acyl-NH, ω-acyl-lysinyl-, ω-acyl-triazole, ω-PEGylcarboxyl-NH—, ω-PEGylcarboxyl-lysinyl, and ω-PEGylcarboxyl-triazole; wherein X is selected from the group consisting of a hydrogen, halogen, CN, Me, $NH_2$, SH and OH; and $R_3$ and $R_4$ are independently a hydrogen, a therapeutic agent, or an imaging moiety, wherein the therapeutic agent is selected from the group consisting of a platinum-based therapeutic agent, a small molecule therapeutic agent, a peptide, a protein, a polymer, an siRNA, a microRNA, and a nanoparticle, wherein the imaging is a radio-isotope selected from the group consisting of F18, I-125, I-124 I-123, I-131, and small molecule labeled with any of these isotopes, or wherein the imaging moiety is a chelator-complexed radioactive isotope, wherein the radioactive isotope is selected from the group consisting of Cu-64. In-111, Tc-99m, Ga-68, Lu-177, Zo-89, Th-227 and Gd-157.

BACKGROUND OF THE INVENTION

Cancer is one of the leading causes of death globally. In 2015, an estimated 1,658,370 new cases of cancer will be diagnosed in the United States and 589,430 people will die from the disease. In the U.S. alone, 1,500 deaths per day are attributed to cancer, which is approximately 1 in every 4 deaths daily. Cancer is also among the leading causes of death worldwide. In 2012, there were 14 million new cases diagnosed and 8.2 million cancer-related deaths worldwide and the number is expected to be 13 million by 2030. Most deaths from cancer are caused by metastasis, for which there is no effective molecular imaging method to detect the tumor and its metastases, nor is there therapy to effectively eradicate the growth of localized and disseminated tumors.

This invention relates to a class of near-infrared (NIR) cyanine-containing dyes. NIR-dyes chemically conjugated with therapeutic drugs (referred to below as NIR dye-drug conjugates), result in effective uptake and retention of NIR dye-drug conjugates in cancer but not normal cells. The specificity of this class of NIR dye-drug conjugates for cancer but not normal cells is based upon the overexpression of membrane carrier proteins, organic anion transporting peptides (OATPs), in cancer, as compared with normal cells. The OATPs-mediated transporting mechanism is further enhanced by tumor hypoxia.

Evidence supporting the role of OATPs in mediating the uptake and retention of NIR dye-drug conjugates in cancer cells is as follows: 1) OATPs are expressed at a higher level in cancer cells, as compared to normal cells; 2) The expression of OATPs is further enhanced by tumor hypoxia, due to the induction of transcription of OATP genes by the enhanced hypoxia-inducing factor 1 (HIF-1α) in cancer cells; 3) The uptake and retention of NIR dye-drug conjugates in tumor cells can be abolished by bromsulphthalein (BSP), a known competitive OATP inhibitor; 4) Because the function of OATPs in cells is energy-dependent as carriers for drugs, metabolites and hormones, the uptake and retention of the NIR dye-drug conjugates by OATPs in cancer cells are also energy-dependent and occur only in live cells; 5) Genetic knockdown of certain isoform of OATPs in cancer cells prevents the uptake and retention of NIR dye-drug conjugates in cancer cells, whereas the overexpression of OATPs in cancer cells enhances the uptake and retention of NIR dye-drug conjugates in cancer cells; and 6) NIR dye-drug conjugates are known to interact with nucleic acids and proteins noncovalently, and, therefore, once the NIR dye-drug conjugates enter into cancer cells, they are trapped in the mitochondrial and lysosomal compartments of the cancer cells.

These results establish the basis for the OATP-based uptake and retention of this class of NIR dye-drug conjugates by tumor cells.

SUMMARY OF THE INVENTION

The current invention is based upon the ability of NIR dye-drug conjugates to be taken up and retained by cancer cells, but not by normal cells, with this action being mediated by OATPs. The chemical entities of the NIR dye-drug conjugates comprise three parts: 1) The NIR dye as a targeting ligand for entering cancer cells through their upregulated OATPs. This targeting ligand (NIR dye) can be imaged by fluorescence, as well as by PET (positron emission tomography) or SPECT (single photon emission computed tomography) after further conjugating the targeting ligand with radionuclides, such as Cu-64, Ga-68, F-18, Tc-99, Lu-177, Zo-89, Th-227 and Gd-157; 2) Therapeutic agents that potentially exhibit self-limiting toxicity, such as gemcitabine and cisplatin; and, 3) A linker connecting the targeting ligand to the therapeutic agents for efficient delivery and/or effective release of therapeutic agents once in the cancer cells.

The present inventor found that NIR dye-drug conjugates can cross cancer cell membranes, blood-brain barrier, bone marrow space, and metastatic solid tumors residing in multiple secondary organ sites resulting from metastasis (such as the lung, the liver, the kidney, the lymph nodes, the brain, the bone, the gastric and digestive system, the intraperitoneal space) and primary tumors residing in the primary organs (such as in the prostate, the lung, the breast, the liver, the colon, the kidney, the bladder, the pancreas, the testes, the ovaries, the brain, the bone marrow, the blood and the digestive system). Due to significant higher levels of NIR dye-drug conjugate uptakes and retentions in cancer cells, as compared with normal cells, embodiments of the invention show the effectiveness of NIR dye-drug conjugates as dual cancer imaging and therapeutic agents for the treatments and diagnosis of human prostate, pancreatic, and brain tumors in mice.

Embodiments of the invention relate to three aspects. First, the inventor identified important structural features of NIR dye-drug conjugates for efficient uptake and retention by cancer cells. By attaching chemical conjugates at different positions of the NIR dyes, the inventor discovered the most favorable position where chemical conjugation is less likely to affect the specificity of transport of the NIR dye-drug conjugates into cancer cells, relative to the normal cells. Second, the inventor selected two commonly used drugs that are known for their self-limiting toxicity, i.e., gemcitabine and cisplatin, to demonstrate the efficacies of chemotherapy using chemical conjugations. This significantly reduced the toxicity of these drugs in mice, increased the effective transport of these drugs into cancer cells mediated by OATPs, and reduced the doses of the drugs yet achieving the same therapeutic effectiveness against the growth of solid tumors. Third, the inventor demonstrated the effectiveness of these NIR dye-drug conjugates in the most deadly human tumors known to cause significant mortality and morbidity in men and currently there is no effectiveness therapy, namely, human prostate and pancreatic cancers, and brain tumors.

BRIEF DESCRIPTION OF THE FIGURES

FIG. 1(C). depicts the chemical structure of DZ-1-cisplatin conjugate developed for targeting cancer therapy in accordance with an embodiment of the present invention.

FIG. 2. Conceptual design of drug-carrier conjugate.

DETAILED DESCRIPTION OF THE INVENTION

Figure 1A:
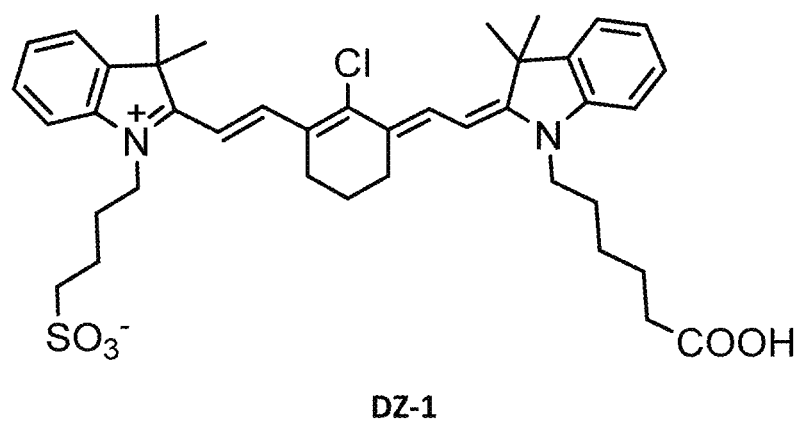
FIG. 1(A). depicts the chemical structure of a cyanine-dye (DZ-1) developed for targeting cancer in accordance with an embodiment of the present invention.

The present invention relates to heptamethine cyanine dyes that act as carrier molecules to specifically deliver drugs to improve the precision of cancer chemotherapy and, with the NIR dye-drug conjugates, these dyes can serve as dual modality imaging and therapeutic agents that can be detected by fluorescent and/or nuclear imaging for cancer diagnosis and treatment follow-up. We have demonstrated certain types of heptamethine cyanine dyes have preferential abilities to target cancer cells when compared with their normal cell counterparts and have the ability to accumulate in the tumors. This preferential uptake of a heptamethine cyanine moiety in tumor is shown to be correlated with enhanced expression of certain types of organic anion transport peptides (OATPs) in variety of cancer cell types, and under the hypoxic microenvironment of tumor. Targeted delivery of variants of theranostic agents to tumor by conjugation with heptamethine cyanine dye has been demonstrated.

The advantages of the invention may include: 1) The heptamethine cyanine dyes specifically target a broad spectrum of cancer cell lines and tumor models, thus can be versatile for conjugation with variety of chemotherapeutic drugs to treat various cancers, and 2) The combined characteristics of imaging and therapeutic (i.e., theranostic) in a single small molecule entity that allows high intracellular accumulation to reduce the toxicity associated with chemotherapy.

The present invention relates to carrier-linker-drug conjugate systems. In accordance with embodiments of the invention, a class of cancer targeting heptamethine cyanine dyes that possess near-infrared (NIR) properties and can act as carrier molecules for targeted drug delivery. The heptamethine dye drug conjugates of the present invention are represented by the following formula:

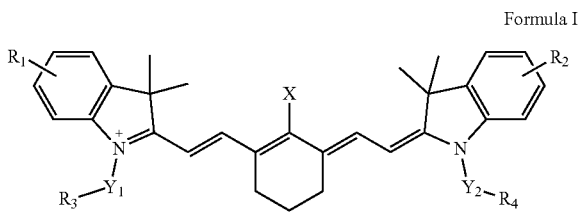

Formula I $R_1$ and $R_2$ can each be independently selected from the group consisting of —H, alkyl, alkyl-sulphonate, alkylcarboxylic, alkylamino, aryl, —$SO_3H$, —$PO_3H$, —OH, —$NH_2$, and -halogen and can be independently attached at the various aromatic ring positions such as 3, 3', 4, 4', 5,5', 6, 6'; any electron withdrawing group (EWG) and electron donating group (EDG) can be independently attached at the various aromatic ring positions.

Side chain $Y_1$ and $Y_2$ can be selected from the group consisting of alkyl, aryl, aralkyl, alkylsulphonate, alkylcarboxylic, alkylamino, ω-alkylaminium, ω-alkynyl, PEGyl, PEGylcarboxylate, ω-PEGylaminium, ω-acyl-NH, ω-acyl-lysinyl-, ω-acyl-triazole, ω-PEGylcarboxyl-NH—, ω-PEGylcarboxyl-lysinyl, ω-PEGylcarboxyl-triazole.

X can be selected from the group consisting of a hydrogen, halogen, CN, Me, $NH_2$, SH and OH.

The heptamethine cyanine dye molecules can be symmetrical ($R_1=R_2$ and $Y_1=Y_2$) or asymmetrical ($R_1 \neq R_2$, $Y_1=Y_2$; $R_1=R_2$, $Y_1 \neq Y_2$; or $R_1 \neq R_2$, $Y_1 \neq Y_2$)

The therapeutic moieties, $R_3$ and $R_4$ can be selected from the group consisting of any therapeutic agents including platinum based agents, small molecules, peptides, proteins, polymers, siRNAs, microRNAs and nanoparticles. The therapeutic agents can be linked with side chain Y through amide bond, ester bond, ether bond, urethane bond, disulfide bond, hydrazone bond or non-covalent interactions, and can be conjugated at one single side ($R_4$ or $R_3$=H) or both sides of the dye side chains.

$R_3$ and $R_4$ can also be an imaging moiety and/or a therapeutic payload, respectively. The imaging moiety can be any of the (1) radio-isotopes including F18, I-125, I-124 I-123, I-131 and small molecule moieties labeled with these isotopes; and (2) chelator complexed radio-metallic isotopes, including Cu-64, In-111, Tc-99m and Ga-68 moieties.

As used herein, "an imaging and/or therapeutic moiety" means that the moiety may function as an imaging agent, a therapeutic agent, and both an imaging and therapeutic agent. Examples of an imaging and therapeutic agent (dual functions) may include radionuclides, which can be imaged by their radiation, while the radiation may also kill cancer cells.

Embodiments of the invention of using heptamethine cyanine dye-drug conjugates as theranostic agents for cancer imaging and therapy have several advantages, which may include one or more of: 1) Well-defined small molecule structural designs with low molecular weights for high reproducibility and consistency, unlike nanomaterials, polymers and biological macromolecules (antibodies); 2) Only two chemical components are needed to provide multifunctional theranostics for simultaneously detection, imaging and therapy without the need for additional chemical components; 3) Cyanine dyes as carriers can target a variety of tumor types and hence the dye-drug conjugates can be as general as they can be for various cancers; 4) a single cyanine dye can be conjugated with multiple equivalent of drugs to further amplify the effectiveness of chemotherapy; and 5) different cyanine dye-drug conjugates can be used in patient or preclinical model in a sequential manner and can be used when resistance is developed for one of the dye-drug conjugate, by switching to a second dye-drug conjugate. An example may be the initial use of DZ-1-gemcitabine conjugate, followed by DZ-1-cisplatin when resistance develops for DZ-1-gemcitabine conjugate. Such sequential treatments should be more effective because of their different mechanisms of action and mechanisms of resistance.

Figure 1B:
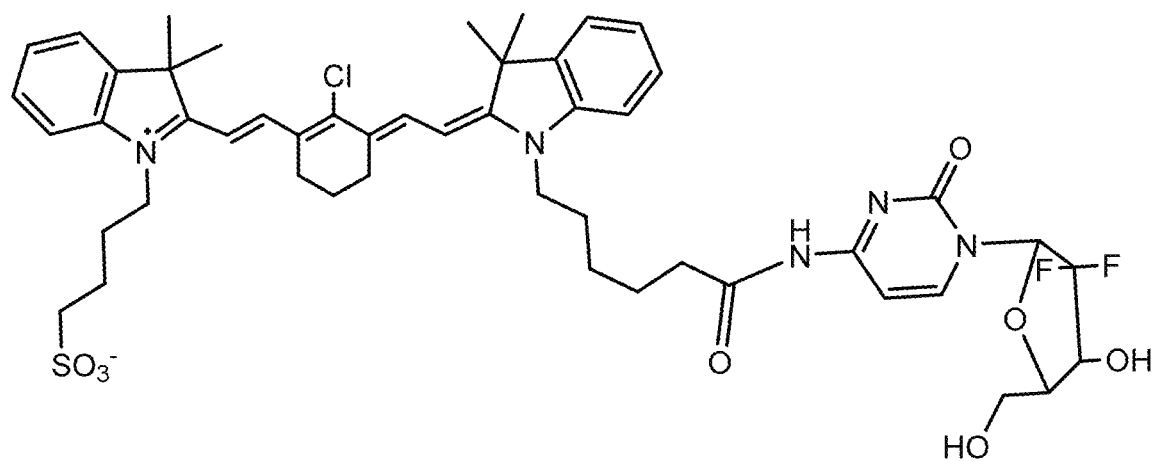
FIG. 1(B). depicts the chemical structure of DZ-1-gemcitabine conjugate developed for targeting cancer therapy in accordance with an embodiment of the present invention.

Embodiments of the present invention also relate to heptamethine cyanine based drug delivery systems for targeted cancer therapy. The dye-drug conjugates of the invention comprise three components: a carrier ligand, an imaging and/or therapeutic agent, and a linker that connects the ligand to the imaging and/or therapeutic agent. FIG. 1 shows some examples of such compounds: a heptamethine cyanine dye (DZ-1), and two dye-drug conjugates.

A heptamethine cyanine dye-based targeting ligand generally comprises a polyene bridge/system that connects two indole analogs on both ends of the polyene system. Electron withdrawing groups or electron donating groups may be added to the targeting ligands. These targeting ligands are cyanine dye analogs and near-infrared emission dyes. These targeting ligands have wavelengths of maximum fluorescence emission ranging from 650-900 nm. The targeting ligands may comprise two to four conjugated double bonds (i.e., a polyene system) and two indole analog structures.

In accordance with embodiments of the invention, therapeutic drugs may be conjugated to the heptamethine cyanine carrier moieties via suitable linkers. The linker modules may comprise alkyl, aromatic group, peptide linkage with single or multiple amino acids and or hydrophilic polyethylene glycol (PEG) moiety to optimize solubility and clearance properties. The drugs may be conjugated to the terminus of a linker through any appropriate functional groups. The functional groups on the ligands or drugs, for example, may include halogen atoms, COOH, $NH_2$, OH, SH succinic ester, nitrile, alkyne, hydrazine, azide, aldehyde, ketone, sulfonic acid, phosphoric acid, alkyl, aromatic group, ester, amide, urea, thiourea, imidazole, thioester, acrylate, thiol ether, dithioate, selenide and phenyl selenide, diene, diketone, pyrimidine, purine and other hetrocyclic ring structure and any radioactive atom or chelator for those atoms (e.g., for PET/SPECT/MRI imaging applications).

The therapeutic drugs, which may be used in the conjugates in accordance with embodiments of the invention, can be any therapeutic agents that can be linked to a targeting ligand, such as platinum-based agents (cisplatin, carboplatin, oxaliplatin, satraplatin, picoplatin and their derivatives), small molecules, photosensitizers, peptides, proteins, polymers, nucleic acids (siRNAs, microRNAs), or nanoparticles.

The multifunctional agents in accordance with embodiments of the present invention for therapy and/or diagnosis may be represented by the following formula I:

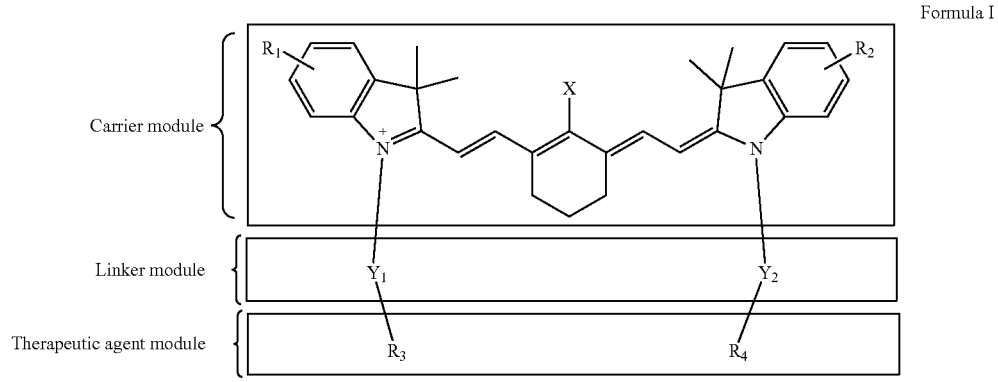

Formula I

Wherein $R_1$ and $R_2$ are each selected from the group consisting of —H, alkyl, alkyl-sulphonate, alkylcarboxylic, alkylamino, aryl, —$SO_3H$, —$PO_3H$, —OH, —$NH_2$, and -halogen, and can be independently attached at the various aromatic ring positions such as 3, 3', 4, 4', 5,5', 6, 6'; any electron withdrawing group (EWG) and electron donating group (EDG) can be independently attached at the various aromatic ring positions.

Wherein the side chains $Y_1$ and $Y_2$ can be selected from the group consisting of alkyl, aryl, aralkyl, alkylsulphonate, alkylcarboxylic, alkylamino, ω-alkylaminium, ω-alkynyl, PEGyl. PEGylcarboxylate, ω-PEGylaminium, ω-acyl-NH, ω-acyl-lysinyl-, ω-acyl-triazole, ω-PEGylcarboxyl-NH—, ω-PEGylcarboxyl-lysinyl, and ω-PEGylcarboxyl-triazole.

As used herein, the terms "alkyl," "alkenyl" and the prefix "alk-" are inclusive of both straight chain and branched chain groups and of cyclic groups, such as cycloalkyl and cycloalkenyl. Unless otherwise specified, these groups may contain from 1 to 20 carbon atoms, with alkenyl groups containing from 2 to 20 carbon atoms. Preferred groups may have a total of up to 10 carbon atoms. Examples of an alkyl group may include $C_1$-$C_6$ alkyl (i.e., an alkyl group with 1-6 carbons), such as methyl, ethyl, propyl, butyl, pentyl, hexyl, etc. Examples of an alkenyl group may include C2-C6 alkenyl (i.e., an alkenyl with 2-6 carbons), such as ethenyl, propenyl, butenyl, etc.

"PEGyl" refers to a polyethylene glycol (PEG) chain comprising a repeated moiety of (—$CH_2$—$CH_2$—O—)$_n$, wherein n is an integer ranging from 2 to 20.

Wherein X is selected from the group consisting of hydrogen, halogen, CN, Me, $NH_2$, SH and OH.

Wherein one of $R_3$ and $R_4$ may be a therapeutic moiety and the other is H, or alternatively both $R_3$ and $R_4$ are therapeutic moieties, wherein the therapeutic moiety may be selected from the group consisting of platinum-based agents, small molecules, peptides, proteins, polymers, siRNAs, microRNAs, and nanoparticles. The therapeutic agents may be linked with a linker $Y_1$ or $Y_2$ via any suitable group, such as an amide bond, ester bond, ether bond, urethane bond, disulfide bond, hydrazone bond, or non-covalent interactions. In some embodiments (either $R_4$ or $R_3$=H), a therapeutic moiety is coupled via a linker to one of the indole analogs, while in other embodiments, the therapeutic moieties are coupled via two linkers to both indole analogs.

In some embodiments, $Y_1$ and/or $Y_2$ can be linked to a platinum-based therapeutic agent through metal-mediated amine-to-nitrile addition forming a cisplatin nitrile complex, or via an ester or amide bond forming cisplatin prodrug.

The platinum-based agents, for example, may be cisplatin, carboplatin, oxaliplatin, satraplatin, picoplatin or their derivatives.

In some embodiments, one of $R_3$ and $R_4$ may be an imaging moiety and the other of $R_3$ and $R_4$ is a therapeutic payload. The imaging moiety, for example, can be any of (1) a radio-isotope including F-18, I-125, I-124 I-123, I-131, or a small molecule moiety labeled with any of these isotopes; and (2) a chelator-complexed Cu-64, In-111, Tc-99m, Ga-68, Lu-177, Zo-89, Th-227 and Gd-157 moiety.

In some embodiments, a chelator for Cu-64 may be selected from the group consisting of: DOTA, NOTA, CBTE-2A, DiAmSar, TETA, Cyclen, Cyclam, and CBTE-2P.

In some embodiments, a chelator for Tc-99m can be selected from the group consisting of: HYNIC, MAG3, MAS3, and CE-DTS.

In some embodiments, a chelator for In-111 may be selected from the group consisting of: DTPA, DOTA, NOTA, and EDTA.

In some embodiments, a chelator for Ga-68 may be selected from the group consisting of: DTPA. DOTA, NOTA, and EDTA.

In some embodiments, a chelator for Lu-177 may be selected from the group consisting of: DTPA, DOTA, NOTA, and EDTA.

In some embodiments, a chelator for Zo-89 may be selected from the group consisting of: DTPA, DOTA, NOTA, and EDTA.

In some embodiments, a chelator for Th-227 may be selected from the group consisting of: DTPA, DOTA, NOTA, and EDTA.

In some embodiments, a chelator for Gd-157 may be selected from the group consisting of: DTPA, DOTA, NOTA, and EDTA.

In some embodiments of the invention, the heptamethine cyanine-based theranostic (i.e., therapeutic and diagnostic) agents may be selected from the group consisting of:

DZ-2
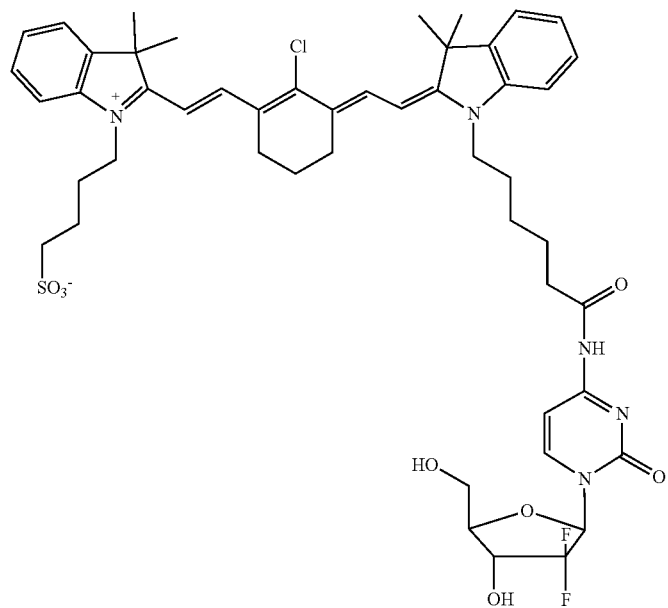
DZ-3
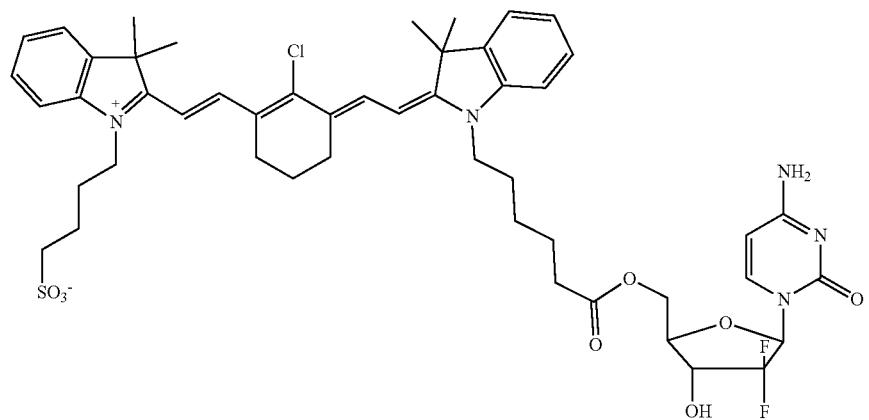
DZ-4
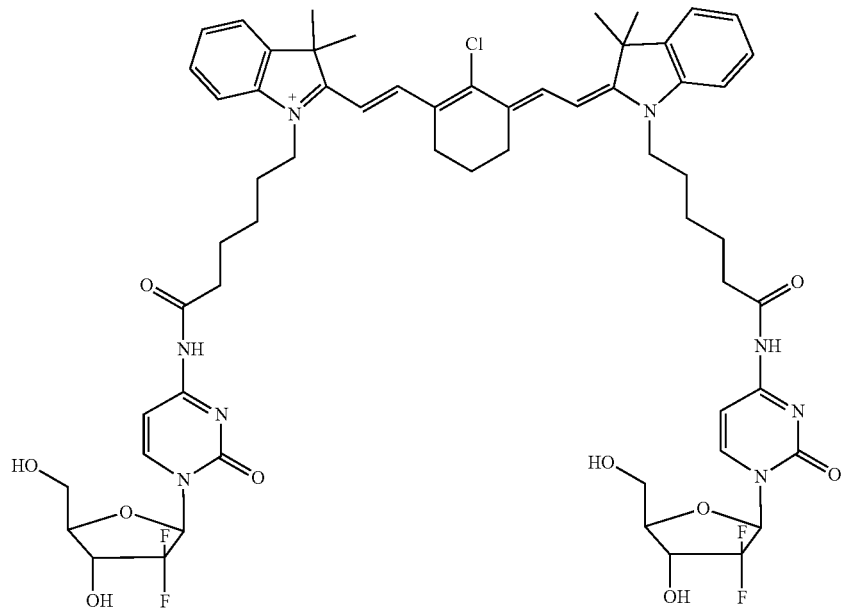

-continued
DZ-5
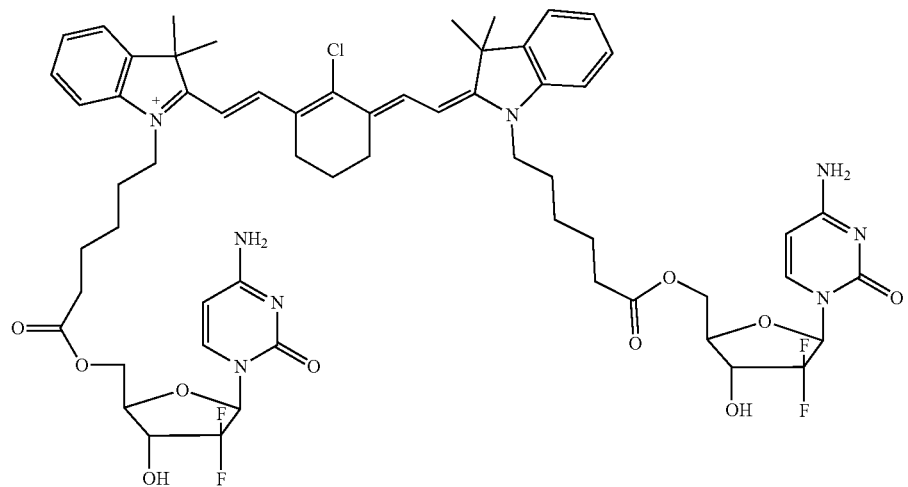
DZ-6
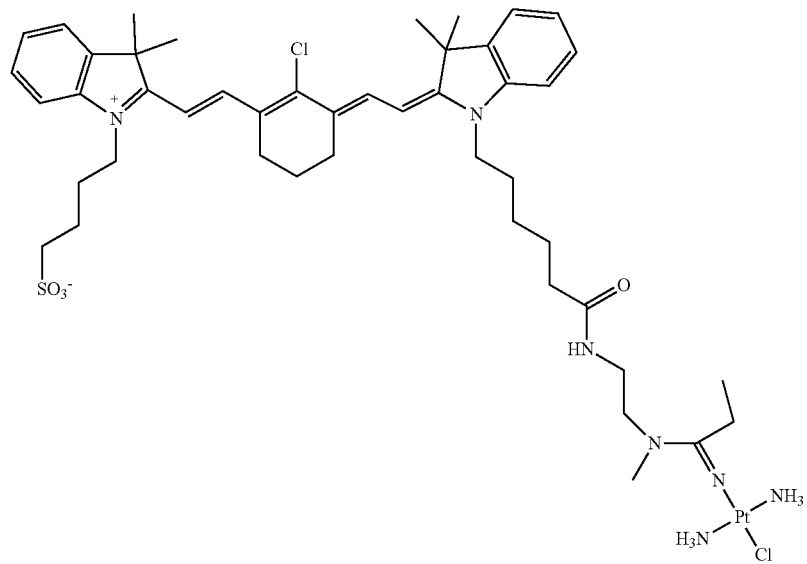
DZ-7
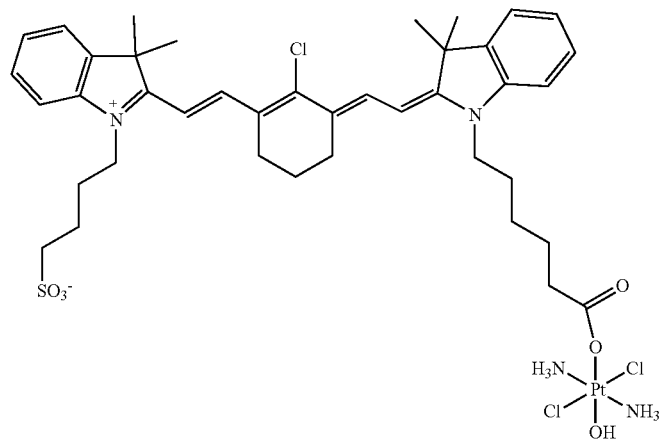

-continued
DZ-8
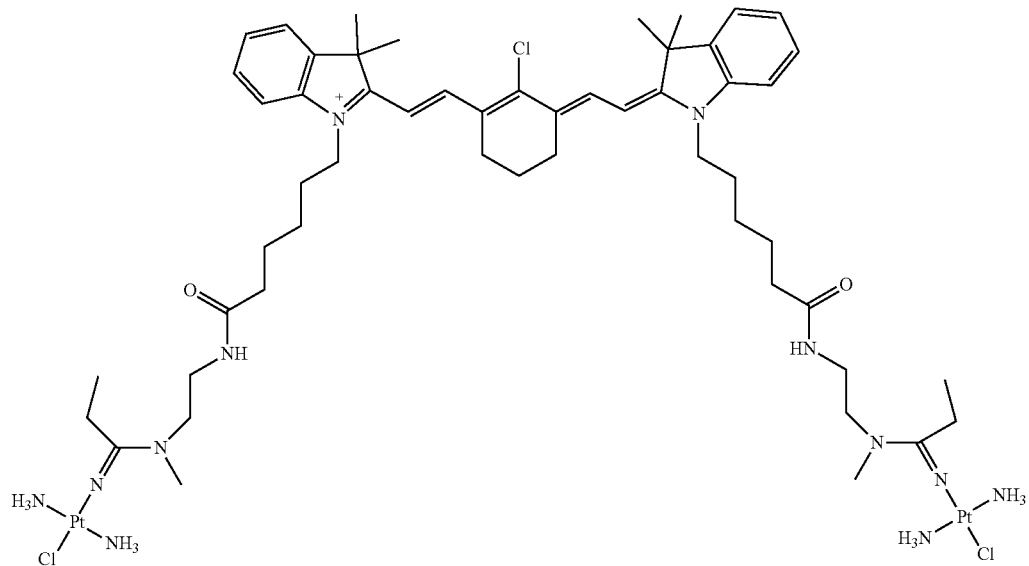
DZ-9
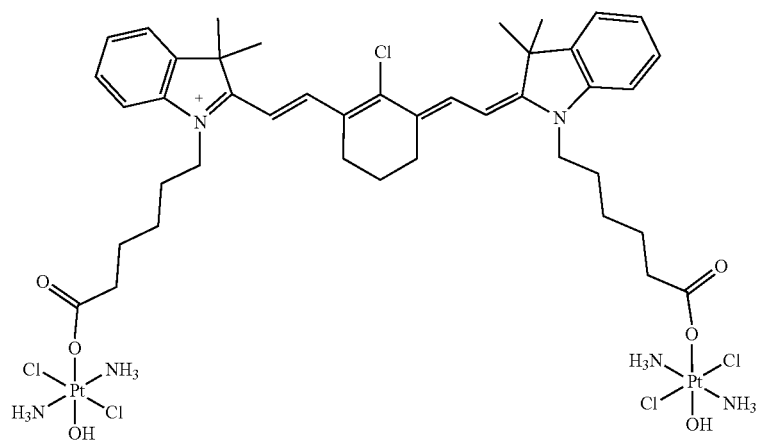
DZ-10
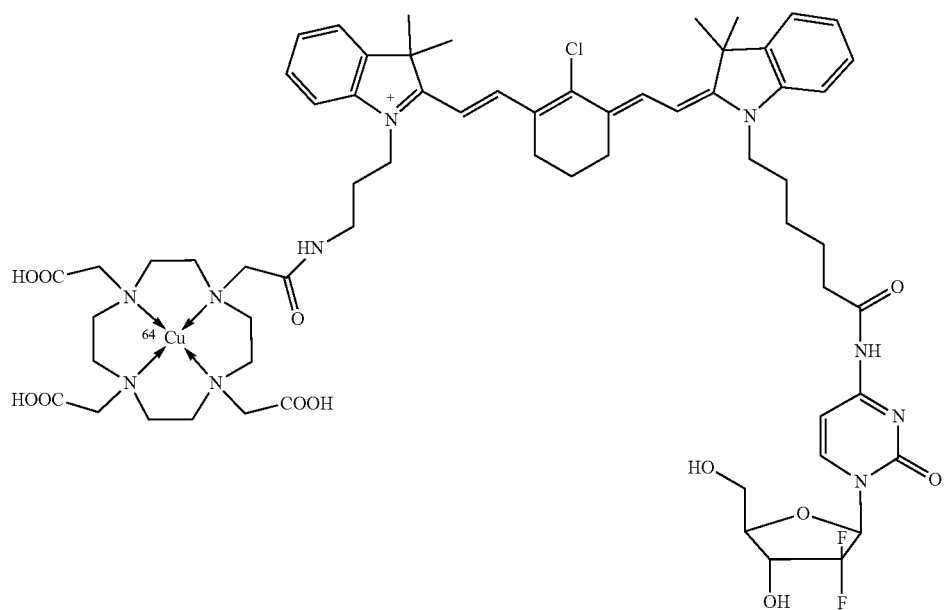

-continued
DZ-11
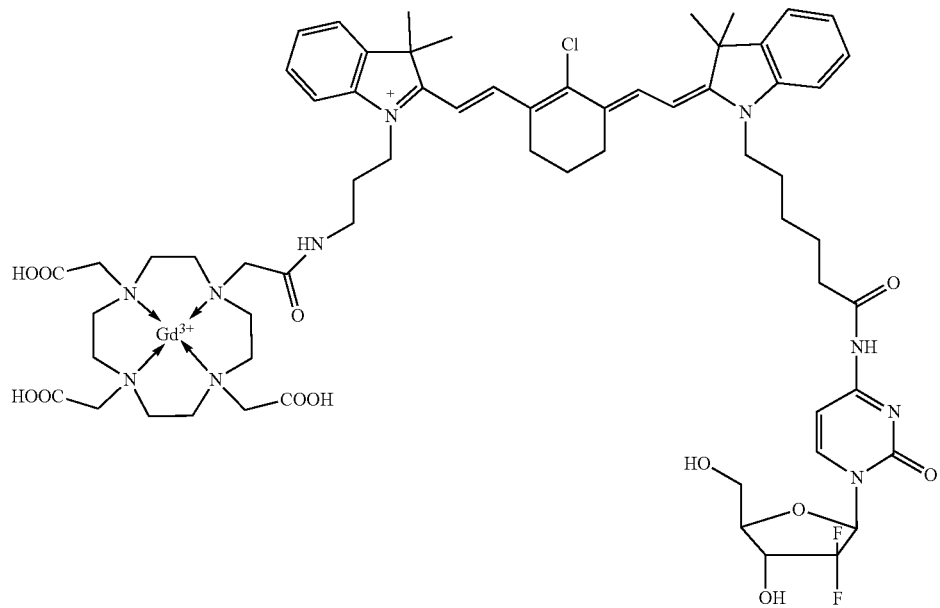
DZ-12
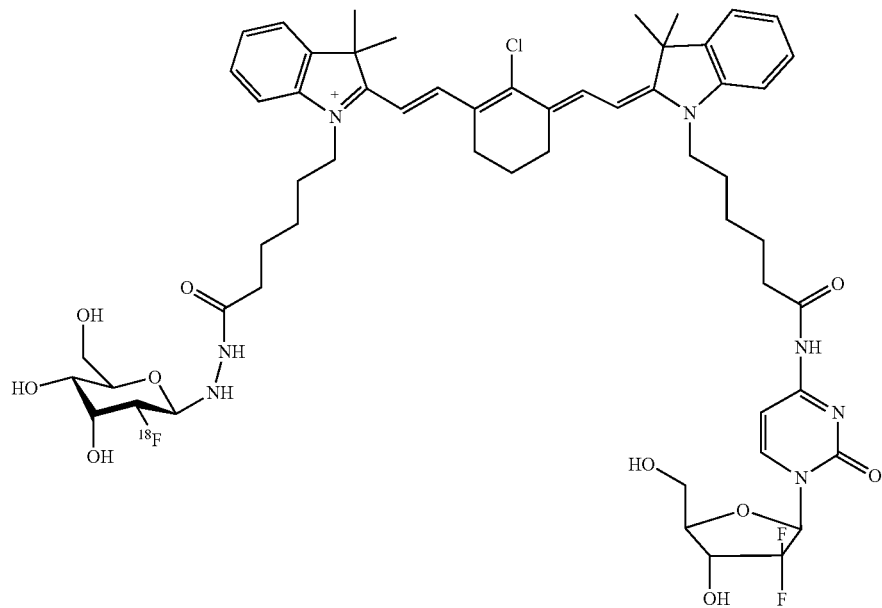
DZ-13
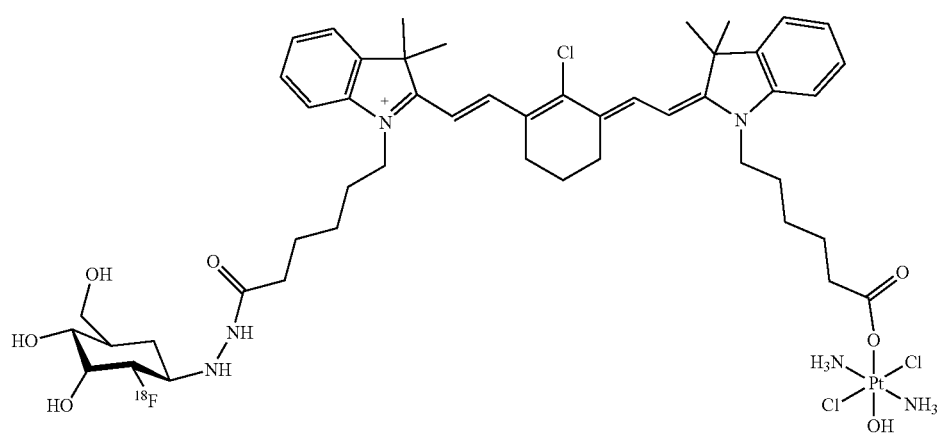

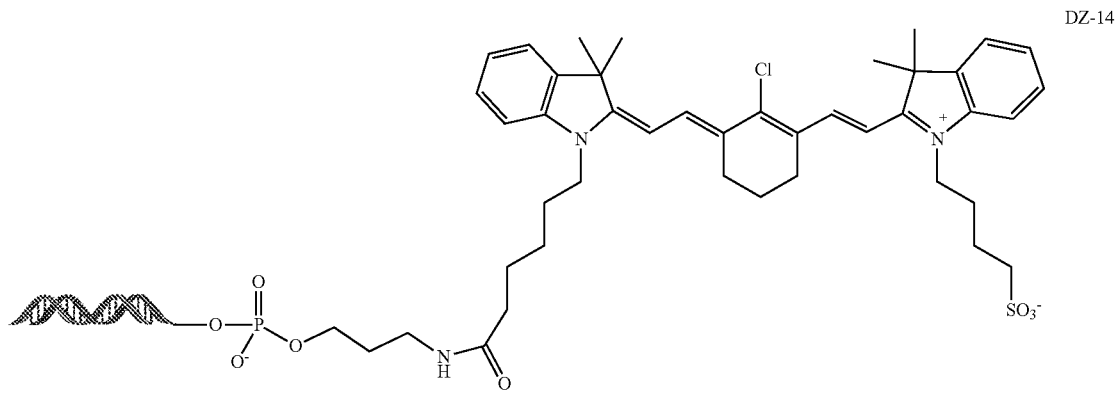

DZ-14

The siRNA-based therapeutic agents may be conjugate at the 3'- and/or 5'-terminus of the sense strand or the 3'-terminus of the antisense strand, via an ester or amide bond. Small interfering RNA (siRNA), also known as short interfering RNA or silencing RNA, is a class of double-stranded RNA molecules, typically of 20-25 base pairs long. However, for use with embodiments of the invention an siRNA may be longer. One skilled in the art would know that a longer sequence may function as a precursor that can be cleaved in vivo to form a proper length siRNA.

The inventor synthesized several heptamethine cyanine dye derivatives (Table 1) and evaluated the tumor specific uptake using Nuclear/NIR imaging. It was unexpectedly found that only certain types of heptamethine cyanine dyes with a halogen (e.g., chloro) atom at the central meso position of the cyclohexyl ring are surprisingly effective in cancer cell targeting.

TABLE 1

Chemical structural features of heptamethine cyanine dye derivatives that have been tested for in vivo cancer targeting

| Cyanine dye derivatives | Cancer targeting |
|---|---|
| 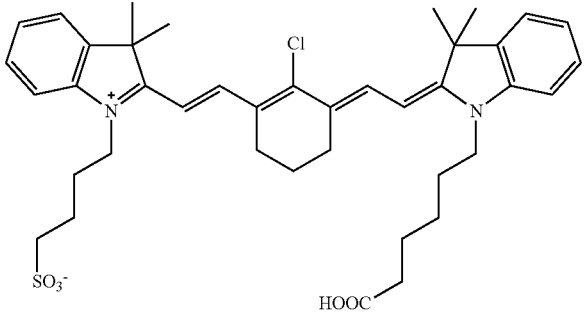 | Positive |

TABLE 1-continued
Chemical structural features of heptamethine cyanine dye derivatives that have been tested for in vivo cancer targeting
| Cyanine dye derivatives | Cancer targeting |
|---|---|
| 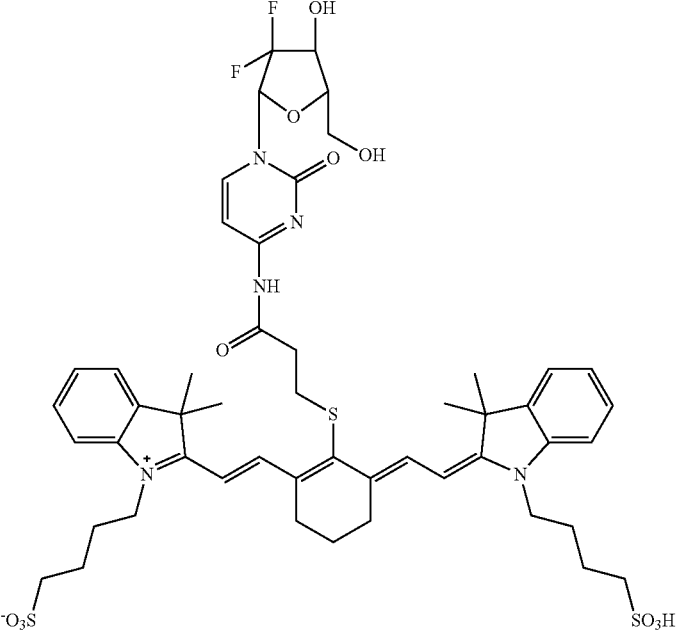 | Negative |
| 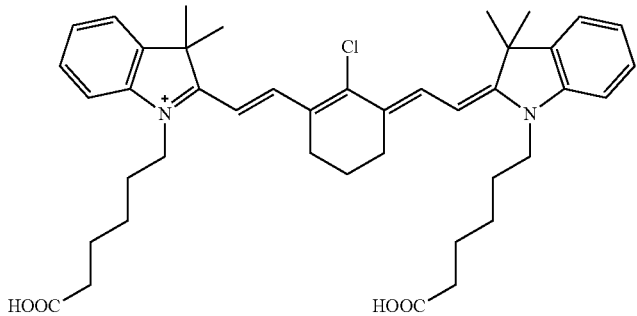 [SMILES: CC1(C)C(/C=C/C2=C(Cl)C(=C/C=C3/N(CCCCCC(=O)O)c4ccccc4C3(C)C)/CCC2)=[N+](CCCCCC(=O)O)c2ccccc21] | Positive |
| 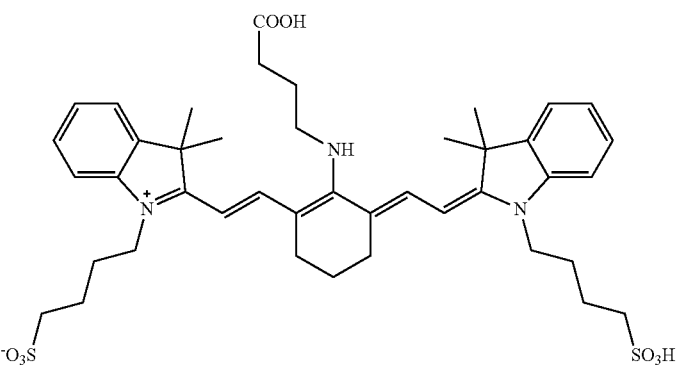 | Negative |

TABLE 1-continued
Chemical structural features of heptamethine cyanine dye derivatives that have been tested for in vivo cancer targeting
| Cyanine dye derivatives | Cancer targeting |
|---|---|
| 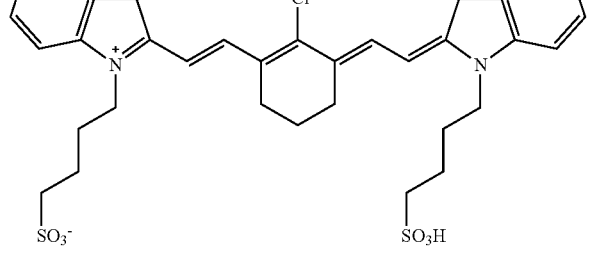 | Positive |
| 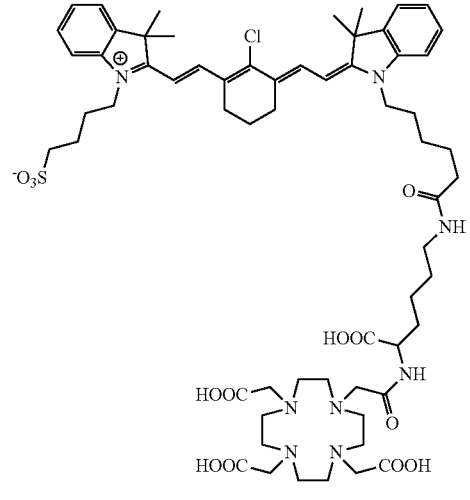 | Positive |
| 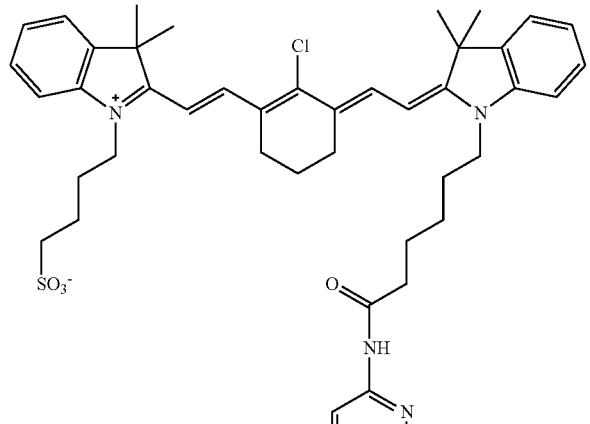 | Positive |

TABLE 1-continued

Chemical structural features of heptamethine cyanine dye derivatives that have been tested for in vivo cancer targeting

| Cyanine dye derivatives | Cancer targeting |
|---|---|
| (structure) | Positive |
| (structure) | Negative |
| (structure) | Positive |

Synthesis of Ligand-Drug Conjugates

Scheme 1 (below) shows the general steps in a synthesis method for dye-gemcitabine conjugates in accordance with embodiments of the invention.

Scheme 2 (below) shows the general steps in a synthesis method for dye-cisplatin conjugates in accordance with embodiments of the invention.

EXAMPLES

Gemcitabine was purchased from Ark Pharm, Inc. (Libertyville, IL). Cisplatin was purchased from Arcos Organics (Morris Plains, NJ). N-BOC-N-methylethylenediamine was purchased from Ark Pharm, Inc. (Libertyville, IL). N-((2-Chloro-3-((phenylimino)methyl)cyclohex-2-en-1-ylidene)

methyl)aniline was purchased from Oxchem Corporation (Irwindale, CA). All other chemicals were purchased from Sigma-Aldrich Chemical Co (St. Louis, MO). Analytical HPLC was conducted on an Agilent 1260 system equipped with pumps, a fraction collector, a 1260 Infinity Diode-Array Detector, using an Alltech Apollo C18 analytical column (5 µm, 150×4.6 mm). Two mobile phases were used for HPLC: Solvent A (0.1% TFA in water) and Solvent B (0.1% TFA in 80% aqueous acetonitrile). The mobile phase gradient varied from 40% of B to 100% of B over a period of 20 minutes, and eluents were monitored at 254 nm (a flow rate of 1 mL/min). ESI-TOF-MS analysis was performed on compounds using a Waters LCT Premier Mass Spectrometer. Proton nuclear magnetic resonance ($^1$H NMR) spectra were recorded on a Bruker AV400 FT NMR Spectrometer (400 MHz).

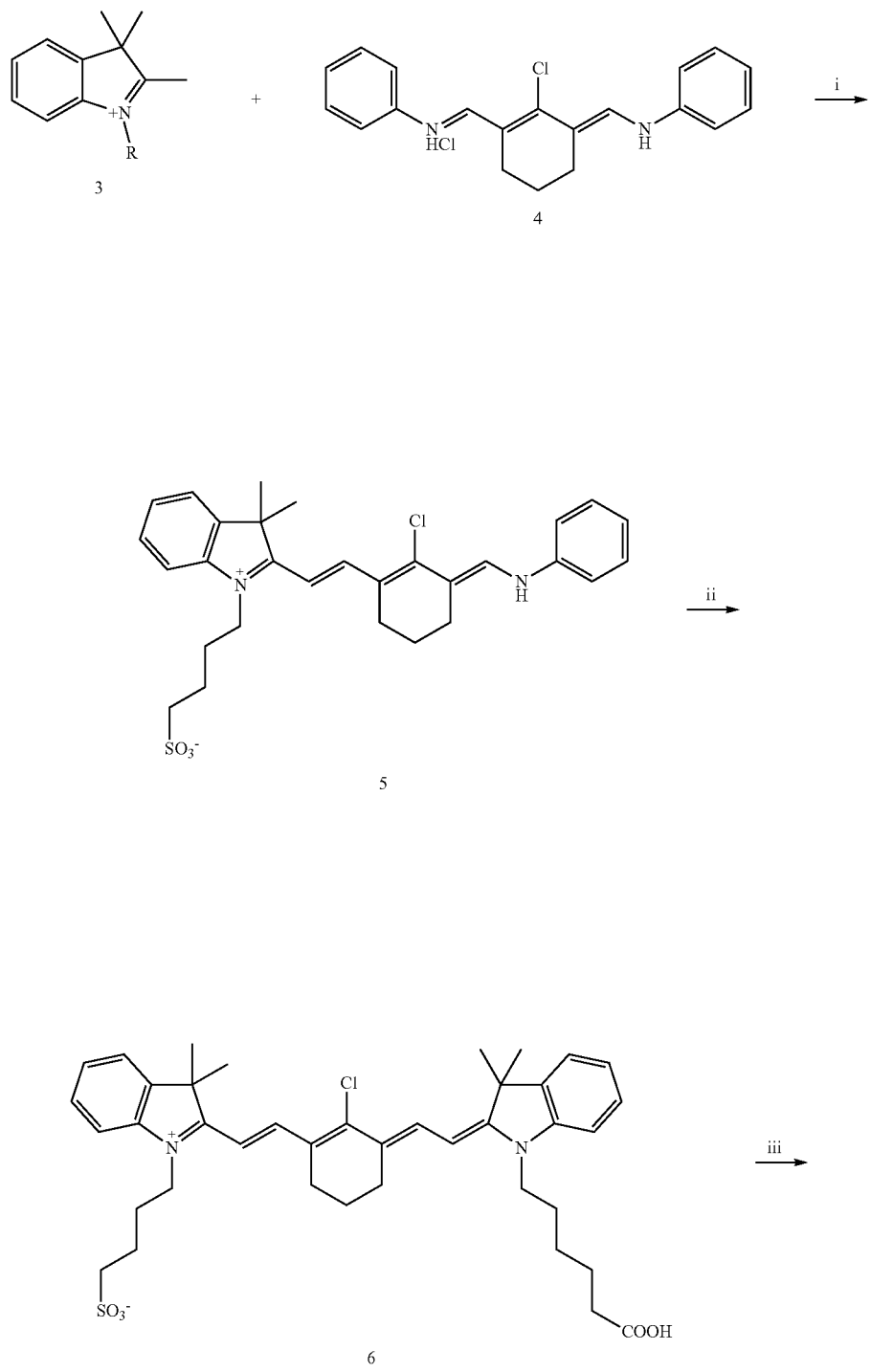

-continued

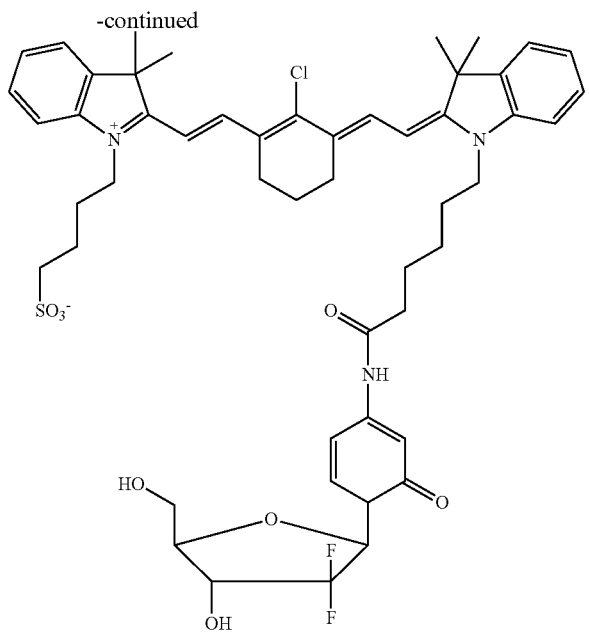

3a: R = ―(CH$_2$)$_4$SO$_3$H
3b: R = ―(CH$_2$)$_5$COOH

Reagents and conditions: (i) 1a, NaOAc, EtOH, reflux, 3 h; (ii) 1b, NaOAc, EtOH, reflux, 3 h; (iii) Gemcitabine, EDC, HOBt, DMF, 15 h.

Example 1

IR-783-Gemcitabine (NIRG) Synthesis:

Synthesis of compound 5: To the mixture of 1a (2 g, 6.78 mmol) and Vilsmeier-Haack reagent 4 (3 g, 8.36 mmol) in EtOH (50 ml) was added CH$_3$COONa (0.56 g, 6.78 mmol). The resulting mixture was heated under reflux for 3 h. The reaction mixture was concentrated, and the residue was recrystallized from methanol-ether to afford the desired product 5 as a dark blue solid (2 g, yield 56%). $^1$H NMR (DMSO-d6, 400 MHz) δ 10.20 (s, 1H), 8.43 (d, 1H, J=16 Hz), 8.19 (s, 1H), 7.71 (m, 2H), 7.53-7.39 (m, 6H), 7.16 (m, 1H), 6.62 (d, 1H, J=12 Hz), 4.38 (m, 2H), 2.71 (m, 4H), 2.52 (m, 2H), 1.87 (m, 4H), 1.75 (m, 2H), 1.69 (s, 6H). MS (ESI-TOF) [M+H]$^+$: 525.1979.

Synthesis of heptamethine cyanine dye 6: To a mixture of 3b (0.5 g, 1.4 mmol) and compound 5 (1 g, 1.9 mmol) in EtOH (20 ml) was added CH$_3$COONa (128 mg, 1.5 mmol). The resulting solution was heated under reflux for 3 h. The reaction mixture was concentrated, and the residue was purified with C18-RP silica chromatography elution with methanol-water to afford the desired product 6 as a dark green solid (0.8 g, yield 73%). $^1$H NMR (DMSO-d6, 400 MHz) δ 11.99 (s, 1H), 8.26 (m, 2H), 7.61-7.22 (m, 8H), 6.43 (d, 1H, J=16 Hz), 6.23 (d, 1H, J=16 Hz), 4.23 (m, 4H), 2.72 (m, 4H), 2.21 (m, 2H), 1.86 (m, 4H), 1.73 (m, 6H), 1.67 (s, 6H), 1.66 (s, 6H), 1.57 (m, 2H), 1.40 (m, 2H). MS (ESI-TOF) [M+H]$^+$: 705.3122.

Synthesis of IR-783-gemcitabine (NIRG) 2: A mixture of 6 (761 mg, 1.1 mmol), 1-ethyl-3-(3-dimethyllaminopropyl) carbodiie hydrochloride (310 mg, 1.6 mmol), and 1-hydroxy-7-azabenzotriazole (175 mg, 1.3 mmol) were dissolved in 5.0 mL DMF. The mixture was stirred for 15 min, and then gemcitabine (340 mg, 1.3 mmol) was added. The resulting mixture was stirred for additional 15 hours. Ethyl ether (50 ml) was added. The precipitates were collected and purified by C18-RP silica chromatography, eluted with methanol-water, to afford the desired product 2 as a dark green solid 509 mg (41%). $^1$H NMR (DMSO-d6, 400 MHz) δ 10.97 (s, 1H), 8.26 (m, 3H), 7.65-7.23 (m, 9H), 6.40 (d, 1H, J=12 Hz), 6.34 (d, 1H, J=8 Hz), 6.22 (d, 1H, J=12 Hz), 5.31 (m, 1H), 4.23 (m, 5H), 3.90 (m, 1H), 3.82 (d, 1H, J=12), 3.67 (d, 1H, J=12), 2.70 (m, 4H), 2.42 (m, 2H), 1.84 (m, 4H), 1.74 (m, 6H), 1.67 (s, 6H), 1.66 (s, 6H), 1.61 (m, 2H), 1.39 (m, 2H). MS (ESI-TOF) [M+H]$^+$: 950.3768.

Scheme 2.

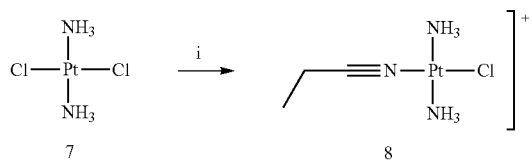

-continued

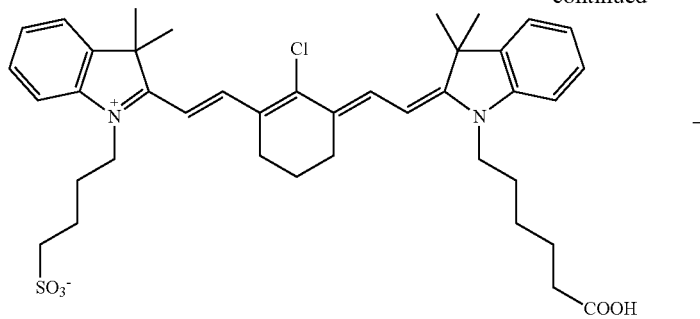

6

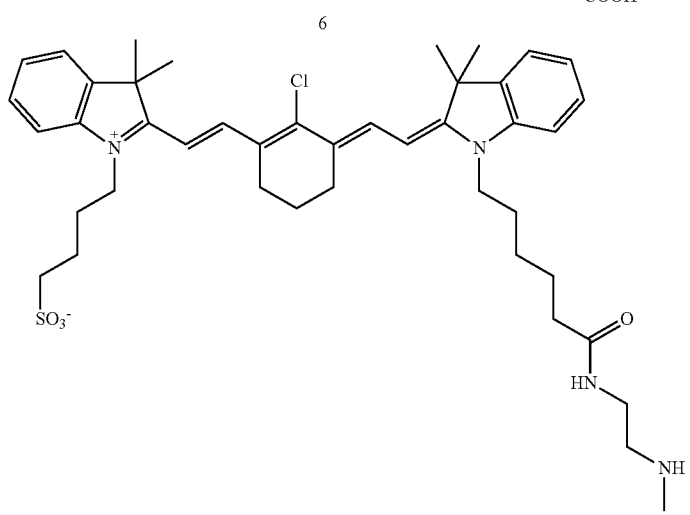

9

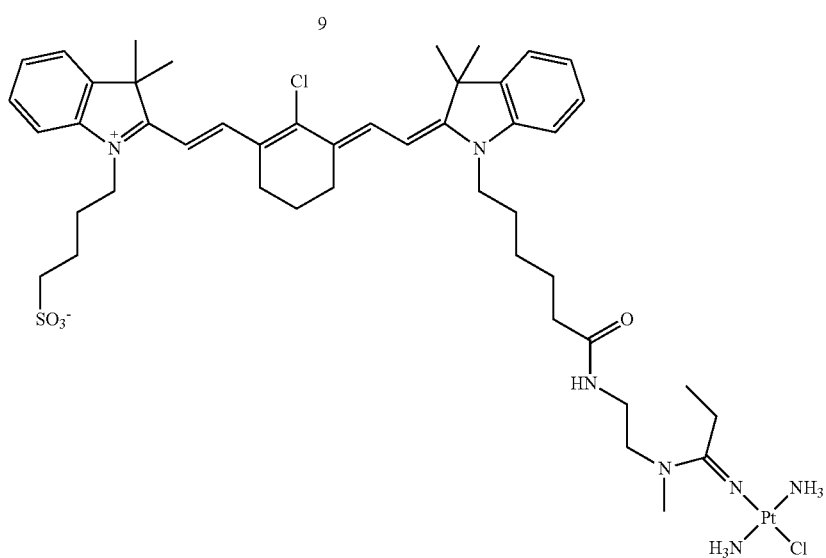

10

Reagents and conditions: (i) HCl, pH4, propionitrile (ii) 1. N-BOC-N-methylethylenediamine, EDC, HOBt, DMF, 15 h; 2. TFA; (iii) cisplatin nitrile complex 2, DMF, 4° C., 5 days

Example 2

The cisplatin nitrile complex 8: A mixture of cisplatin 7 (0.6 g, 2.0 mmol) and propionitrile (8.2 mL, 118.2 mmol) in 30 mL of HCl (pH 4) was heated under reflux for 2 h. The solvent was removed under reduced pressure, and the pale-yellow residue was dissolved in 15 mL of methanol. The solution was filtered and the filtrate was added to 200 mL of ether. The precipitates were collected and dried under vacuum to afford 373 mg 8 (yield: 57%). MS (ESI-TOF) $[M+H]^+$: 320.0271.

Synthesis of IR-783-N1-methylethylenediamine 9: A mixture of 6 (850 mg, 1.2 mmol), 1-ethyl-3-(3-dimethyllaminopropyl) carbodiie hydrochloride (346 mg, 1.8 mmol), and 1-hydroxy-7-azabenzotriazole (195 mg, 1.4 mmol) were dissolved in 10.0 mL DMF. The mixture was stirred for 30 min, and then N-BOC-N-methylethylenediamin (231 mg, 1.7 mmol) was added. The mixture was stirred for additional 18 hours. Ethyl ether (50 ml) was added. The precipitates were collected and purified by C18-RP silica chromatography, eluted with methanol-water, to afford a pure product as a dark green solid.

The product was dissolved in 20 mL of 40% TFA in methylene chloride, and the solution was stirred for 3 h at rt. Ether 100 mL was added. The precipitate was collected and washed with ether and then dried under vacuum to afford the desired product 9, 395 mg (43%). $^1$H NMR (DMSO-d6, 400 MHz) δ 8.38 (br, 2H), 8.21 (m, 2H), 7.97 (t, 1H), 7.60 (m, 2H), 7.49 (d, 1H), 7.40 (m, 1H), 7.36 (s, 2H), 7.26 (m, 2H), 6.41 (d, 1H), 6.23 (d, 1H), 4.19 (m, 4H), 3.25 (t, 2H), 2.88 (m, 2H), 2.68 (m, 4H), 2.52 (m, 4H), 2.05 (t, 2H), 1.81 (m, 4H), 1.70 (m, 4H), 1.63 (s, 6H), 1.62 (s, 6H), 1.54 (m, 2H), 1.32 (m, 2H). MS (ESI-TOF) [M+H]$^+$: 761.3868.

Synthesis of IR-783-N1-methylethylenediamine-cisplatin 10: Cisplatin nitrile complex 8 (355 mg, 1.0 mmol) was converted to its nitrate salt by reaction with AgNO$_3$ (169 mg, 1.0 mmol) in 10 mL of anhydrous DMF for 1 h. The mixture was centrifuged for 10 min. The precipitate was discarded, and the supernatant was cooled to −10° C. IR-783-N1-methylethylenediamine 9 (200 mg, 0.26 mmol) was added to the solution, and the suspension was stirred at 4° C. for 5 days. The reaction mixture was added into 300 mL of diethyl ether. The precipitate was collected and dried under vacuum. The solid was dissolved in methylene chloride and filtered through a 0.45μ glass fiber filter. The solvent was removed under reduced pressure, and the product was dissolved in water and filtered. The aqueous solution was frozen at −20° C. and then lyophilized to give a dark green solid 205 mg (yield: 72%). $^1$H NMR (DMSO-d6, 4(0) MHz) δ 8.21 (m, 2H), 8.04 (t, 1H), 7.60 (m, 2H), 7.48 (d, 1H), 7.41 (d, 1H), 7.38 (d, 2H), 7.25 (m, 2H), 6.39 (d, 1H), 6.24 (d, 1H), 4.20 (m, 4H), 3.25 (m, 2H), 2.94 (q, 2H), 2.87 (m, 2H), 2.69 (m, 4H), 2.50 (m, 4H), 2.06 (t, 2H), 1.81 (m, 4H), 1.70 (m, 4H), 1.63 (s, 6H), 1.62 (s, 6H), 1.54 (m, 2H), 1.32 (m, 2H), 1.18 (t, 3H). MS (ESI-TOF) [M+H]$^+$: 1078.4177.

In accordance with embodiments of the invention, a targeting ligand may comprise an indole analog portion, a polyene portion, and a side chain portion. In accordance with some embodiments of the invention, a targeting ligand may comprise an electron-withdrawing group or an electron-donating group on the indole analog or the polyene portion.

In accordance with embodiments of the invention, the indole portion, the polyene portion, and/or the side chain portion may comprise a conjugation-amenable functional group. Conjugation-amenable functional groups are well known in the art and may include, for example, amino, carboxyl, thiol, —OH, etc. In some embodiments, the conjugation-amenable functional group may be selected from a group consisting of hydroxy, amine, SH, and COOH.

In some embodiments, the therapeutic agent may be selected from a group consisting of: anticancer drugs capable of targeting cell growth, survival, angiogenesis, adhesion, migration, invasion, metastasis, cell cycle progression, the phenotypes of stem cell, neuroendocrine cell, and epithelial mesenchymal transition (EMT), and promoting apoptosis. Therapeutic agents of choice for chemical conjugations may include drugs known to be highly toxic to cancer cells at nanomolar concentrations, drugs having self-limiting toxicity to normal cells, and/or drugs having therapeutic effective doses well tolerated by patients, and combinations thereof.

In some embodiments, the anticancer drug may be selected from a group consisting of: cisplatin, gemcitabine, peptides, siRNAs, and microRNAs.

In some embodiments, therapeutic agents may be a radionuclide that could be alpha, beta, or gamma emitters. The radionuclides may also function as imaging agents.

In some embodiments, the nuclear imaging agents may be detected by PET (positron emission tomography or SPECT (single photon emission computed tomography). Furthermore, such imaging agents may comprise a magnetic resonance imaging (MRI) active nuclide to increase sensitivity and specificity of tumor detection.

Embodiments of the present invention also relate to methods for treating cancer in patients. A method of the invention may comprise: providing a small molecule conjugate compound of the present invention, and administering an effective amount of the compound to a patient in need of such treatments.

Embodiments of the present invention may also relate to methods of sterilizing circulating tumor cells in patients in need thereof. A method of the invention may comprise: providing a small molecule conjugate compound of the present invention, and administering an effective amount of the compound to the patient, wherein subsequent adhesion or extravasation of the cancer cells to form a metastatic deposit is minimized or prevented.

As used herein, "sterilizing circulating tumor cells" means eliminating or minimizing the abilities of the tumor cells to form a metastatic deposit.

Embodiments of the present invention may also relate to methods of imaging cancer cells in the primary and cancer disseminated to distant organs. A method of the invention may comprise: providing a small molecule conjugate compound of the present invention, and administering an effective amount of the compound to a patient in need thereof or to a tissue, wherein the imaging agent is a fluorescent agent or a radionuclide that can be detected by a near-infrared region of the electromagnetic spectrum (from about 700 nm to 2500 nm), nuclear imaging by PET, SPECT, and/or MRI of solid tumors in patients residing in tissues thereof.

Table 2 (below) shows the cytotoxicity, evaluated as IC50, of NIR dye-gemcitabine on the growth of prostate and pancreatic cancer cells in vitro. This table shows the results of the cytotoxicity exerted by the NIR dye-gemcitabine conjugate (or DZ-1-gemcitabine conjugate) on human prostate cancer (LNCaP, C4-2, C4-2B, PC3) and pancreatic cancer (MIA PaCa and BxPC-3) cells grown in culture, in comparison with the parental gemcitabine (unconjugated drug serves as positive control) and the naked dye IR-783 (a negative control) in vitro. We also compared the effectiveness of DZ-1-gemcitabine conjugate with that of NIR dye-docetaxel and NIR dye-clorgyline conjugate in a hope to determine the best NIR dye-drug conjugate that can limit the growth of cultured tumor cells in vitro.

TABLE 2

The dye-docetaxel and dye-gemcitabine conjugates are more effective than dye-clorgyline conjugate in inhibiting the growth of cancer cells.

| $IC_{50}$ in vitro | LNCaP | C4-2 | C4-2B | PC-3 | MiaPaCa II | BX-PC3 |
|---|---|---|---|---|---|---|
| DZ1gemcitabine | 0.34 µM | 0.093 µM | | 0.42 µM | 0.085 µM | 0.230 µM |
| Gemcitabine | 0.25 µM | 0.085 µM | | 0.38 µM | 0.022 µM | 0.135 µM |
| Dye-docetaxel | 3.20 µM | | | 3.60 µM | 4.200 µM | 3.600 µM |
| Docetaxel | 0.01 µM | 3.200 µM | | 0.33 µM | 0.006 µM | 0.007 µM |
| Dye-clorgyline | 5.00 µM | 0.008 µM | 6 µM | 6 µM | | |
| Clorgyline | 81.0 µM | | 114 µM | 120 µM | | |

Note:
the dye moiety, IR783, at 25 µM, showed no inhibitory effect on cancer cell growth (not shown).

Figure 3:
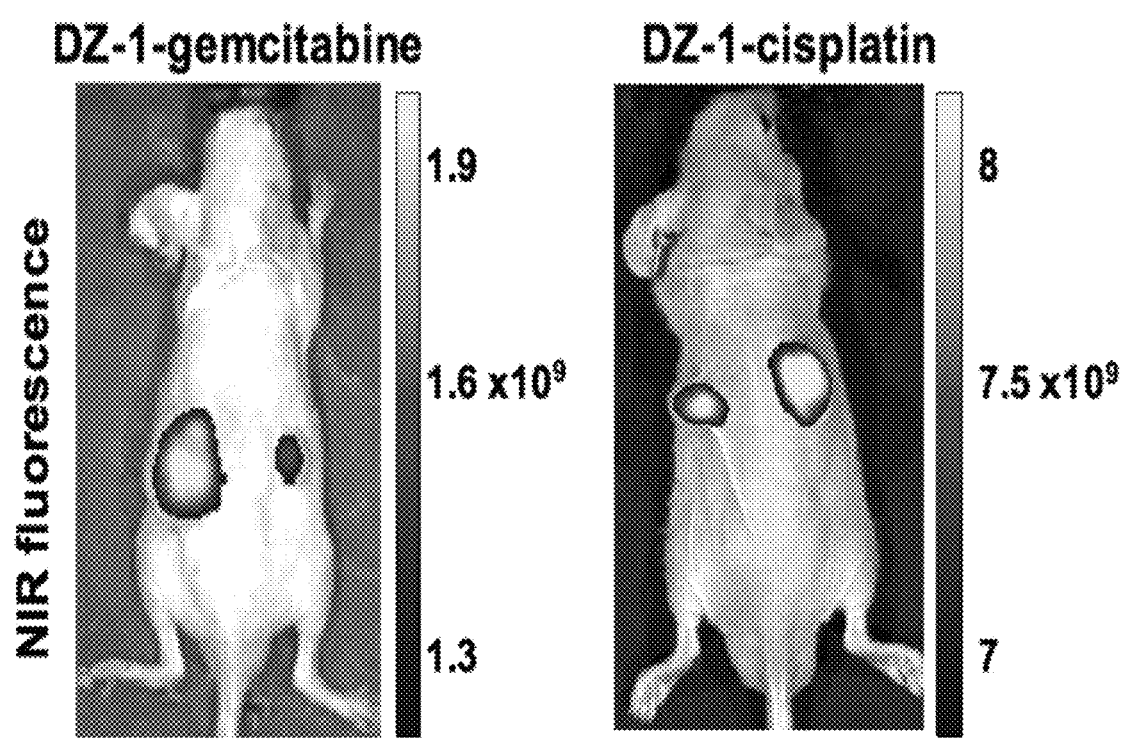
FIG. 3 shows results of uptake of DZ-1-gemcitabine (left panel) and DZ-1-cisplatin (right panel) to prostate cancer PC3 tumors in mice in accordance with one embodiment of the invention.

The uptake of DZ-1-gemcitabine and DZ-1-cisplatin by prostate cancer PC3 tumor cells in mice was investigated. In brief, mice bearing PC3 tumors were administered 100 nmole of DZ-1-gemcitabine and DZ-1-cisplatin, respectively, via i.p. injection, and imaged 48 hours thereafter. Both compounds found to accumulate only in the tumor cells, but not in the normal organs, as shown in FIG. 3.

Figure 4:
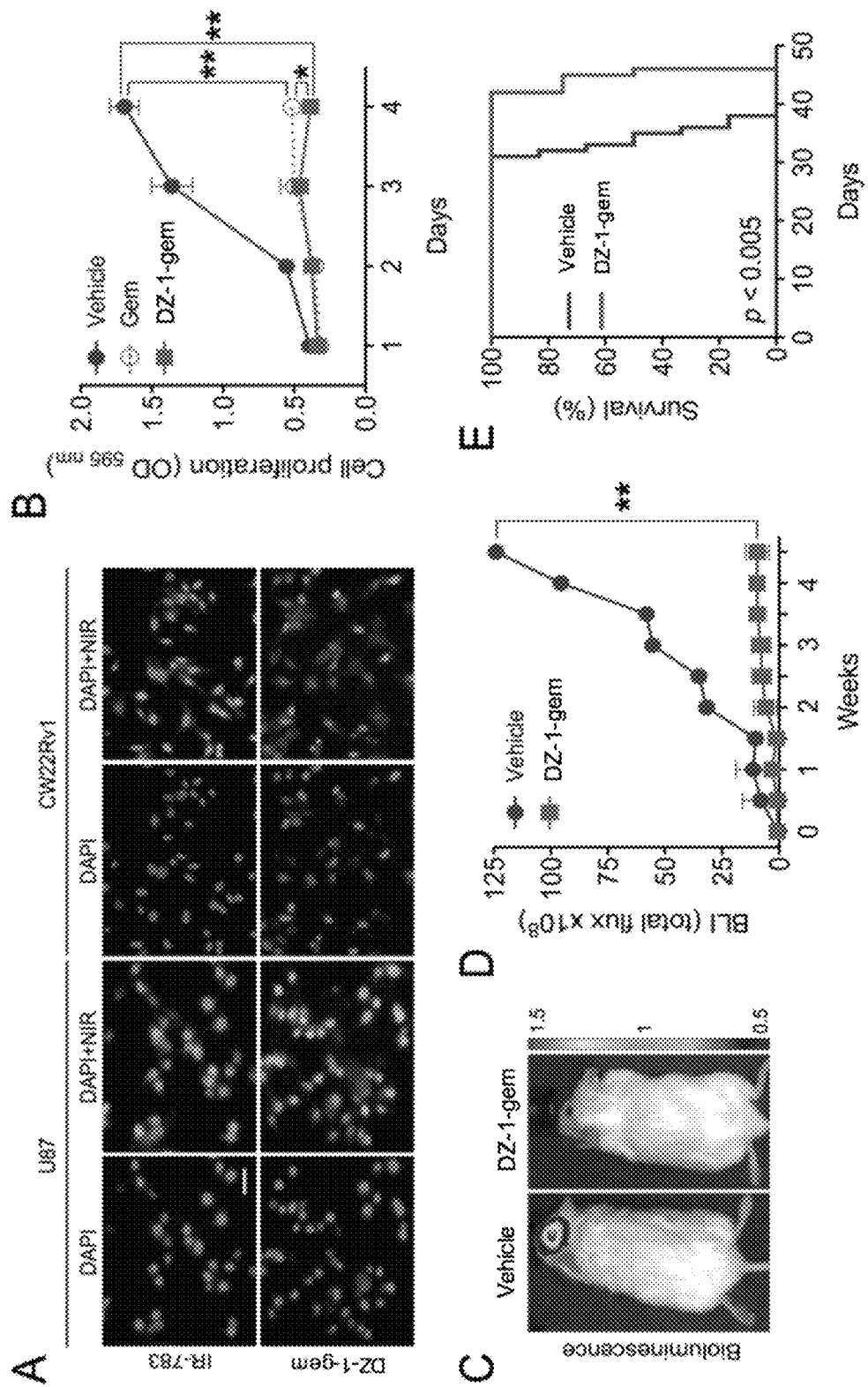
FIG. 4 shows results of characterization of DZ-1-gemcitabine. (A) Uptake of DZ-1-Gem (5 µM, 10 min) by U87 and CW22Rv1 cells. IR-783 was used a positive control in parallel. Scale bar represents 50 µm. (B) Proliferation of U87 cells treated with vehicle, gemcitabine (200 nM) or DZ-1-Gem (200 nM) for 4 consecutive days. Cells were fixed and stained with crystal violet, and OD value at the wavelength of 595 nm was determined (n=5 for each experimental group, mean±SEM) *p<0.05, p<0.01. (C) Representative BLI images of intracranial U87 tumor-bearing mice treated with vehicle or DZ-1-Gem (10 mg/kg, twice a week) (D) BLI curves of U87 tumor growth from each experimental group (n=2, mean±SEM) in (C) p<0.01. (E) Kaplan-Meier survival curve of mice bearing CW22Rv1 prostate tumor brain metastases, which were treated with vehicle (n=6) or DZ-1-Gem (10 mg/kg, twice a week) (n=4) p<0.001 (log-rank test).

The uptakes of DZ-1-gemcitabine ("DZ-1-Gem") in various cancer cells were also invested. As shown in FIG. 4(A), DZ-1-Gem (5 µM, 10 min) is readily taken up by U87 and CW22Rv1 cells. IR-783 was used a positive control in parallel. Scale bar represents 50 µm.

As shown in FIG. 4(B), in proliferation experiments of U87 cells treated with vehicle, gemcitabine (200 nM) or DZ-1-Gem (200 nM) for 4 consecutive days, it was found that DZ-1-Gem is as effective as Gem in inhibiting U87 cell proliferation. In these experiments, cells were fixed and stained with crystal violet, and OD value at the wavelength of 595 nm was determined (n=5 for each experimental group, mean±SEM) *p<0.05, **p<0.01. As shown in FIG. 4(C), representative bioluminescence imaging (BLI images) of intracranial U87 tumor-bearing mice treated with vehicle or DZ-1-Gem (10 mg/kg, twice a week) are shown. It is clear that treatment with DZ-1-Gem effectively suppressed tumor growth, resulting in no bioluminescence.

FIG. 4(D) shows BLI curves of U87 tumor growth from each experimental group (n=2, mean±SEM) in FIG. 4(C). **p<0.01. Mice treated with DZ-1-Gem have significantly improved survival, as evidenced by the Kaplan-Meier survival curves of mice bearing CW22Rv1 prostate tumor brain metastases, treated with vehicle (n=6) or DZ-1-Gem (10 mg/kg, twice a week (n=4), p<0.001 (log-rank test)), as shown in FIG. 4(E).

In addition to DZ-1-Gem, some agents of the invention may include other antitumor active moieties, such as cisplatin. For example, the tumor cell growth inhibition activities of DZ-1 linked with cisplatin ("DZ-1-cisplatin") were compared with those of cisplatin alone in various tumor cells, including prostate, breast, renal, kidney, and lung cancer cell lines. As shown in Table 3, DZ-1-cisplatin is more effective than cisplatin in inhibiting several tumor cells in vitro, including LNCaP, C4-2, and H358 tumor cells.

TABLE 3

$IC_{50}$ of cisplatin and DZ-1-cisplatin on prostate, breast, renal, kidney, and lung cancer cell lines.

| | Half maximal inhibitory concentration ($IC_{50}$) | | |
|---|---|---|---|
| Cell lines | Cisplatin | Dye-Cisplatin | p value |
| Prostate Cancer | | | |
| PC3 | >50 µM | 7.57 µM | p = 0.23 |
| LNCaP | >50 µM | 21.6 µM | p = 0.0002 |
| C4-2B | >50 µM | 15.94 µM | P < 0.001 |
| Breast Cancer | | | |
| MCF-7 | 14.99 µM | 13.12 µM | p = 0.94 |
| Renal Cancer | | | |
| ACHN | 28.74 µM | 4.034 µM | p = 0.13 |
| Hepatic Cancer | | | |
| Hep G2 | >50 µM | >50 µM | p = 0.97 |
| Lung Cancer | | | |
| H358 | >50 µM | 4.95 µM | p = 0.001 |

Figure 5:
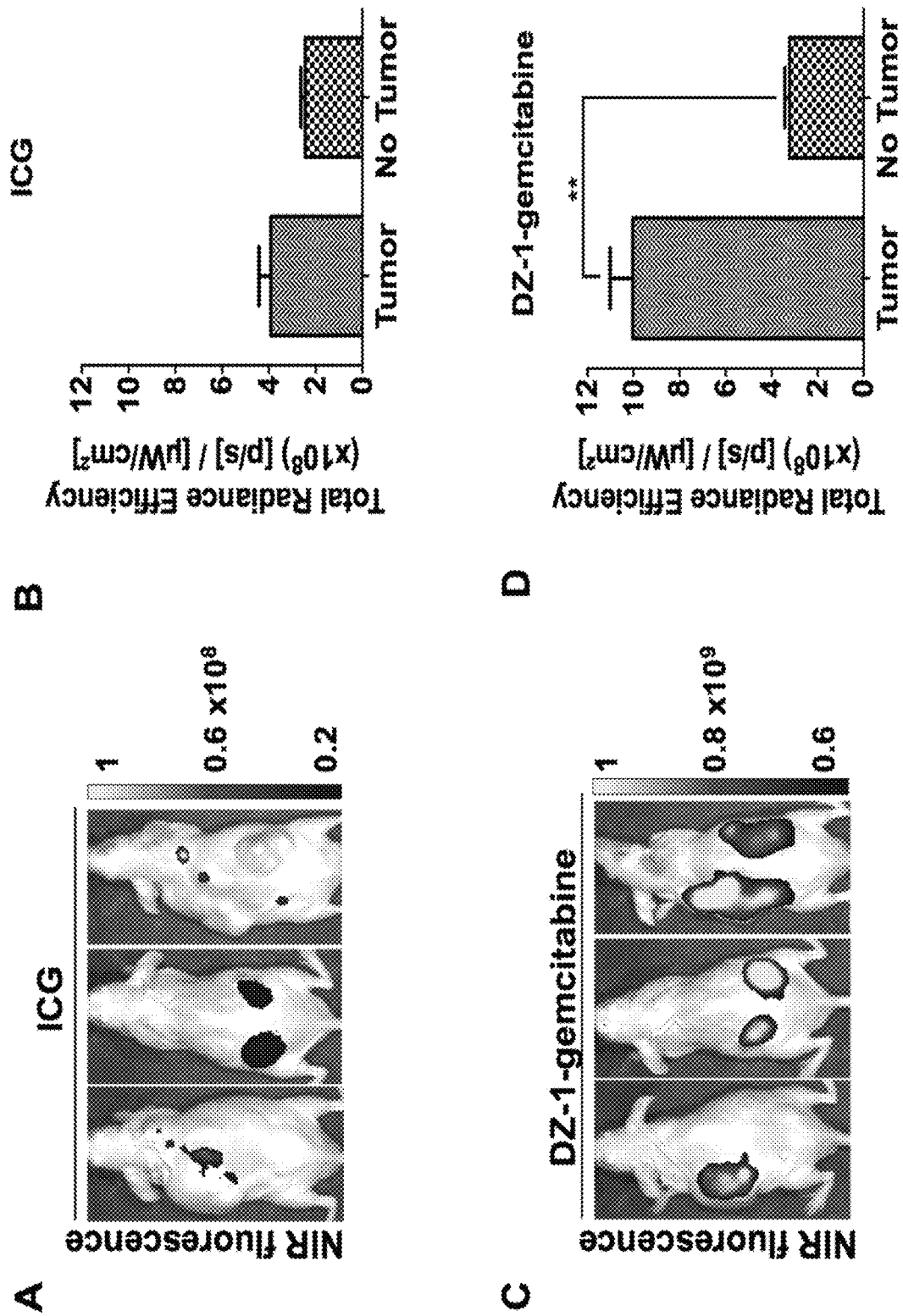
FIG. 5 shows results of uptake of indocyanine green (ICG) and DZ-1-gemcitabine by pancreatic MIAPaCa subcutaneous tumors. (A) Representative NIR fluorescent imaging of mice bearing MIAPaCa subcutaneous tumors two days after ICG injections (7.2 mg/kg, i.p.) (B) Quantitative analysis of IGC uptake intensity in total radiance efficiency of tumors and areas with no tumor (n=3) (C) Representative NIR fluorescent imaging of mice bearing MIAPaCa subcutaneous tumors two days after DZ-1-gemcitabine injections (10 mg/kg, i.p.) (D) Quantitative analysis of DZ-1-gemcitabine uptake intensity in total radiance efficiency of tumors and areas with no tumor (n=3) *p<0.05;  p<0.01; * p<0.001.

The uptakes of indocyanine green (ICG) and DZ-1-gemcitabine by pancreatic MIAPaCa subcutaneous tumors were also investigated. FIG. 5(A) shows representative NIR fluorescent imaging of mice bearing MIAPaCa subcutaneous tumors two days after ICG injections (7.2 mg/kg, i.p.). FIG. 5(B) shows the quantitative analysis of ICG uptake intensities in total radiance efficiency of tumors and areas with no tumor (n=3). FIG. 5(C) shows representative NIR fluorescent imaging of mice bearing MIAPaCa subcutaneous tumors two days after DZ-1-gemcitabine (DZ-1-Gem) injections (10 mg/kg, i.p.). FIG. 5(D) shows the quantitative analysis of uptake intensities in total radiance efficiency of tumors and areas with no tumor (n=3). * p<0.05;  p<0.01; * p<0.001.

Figure 6:
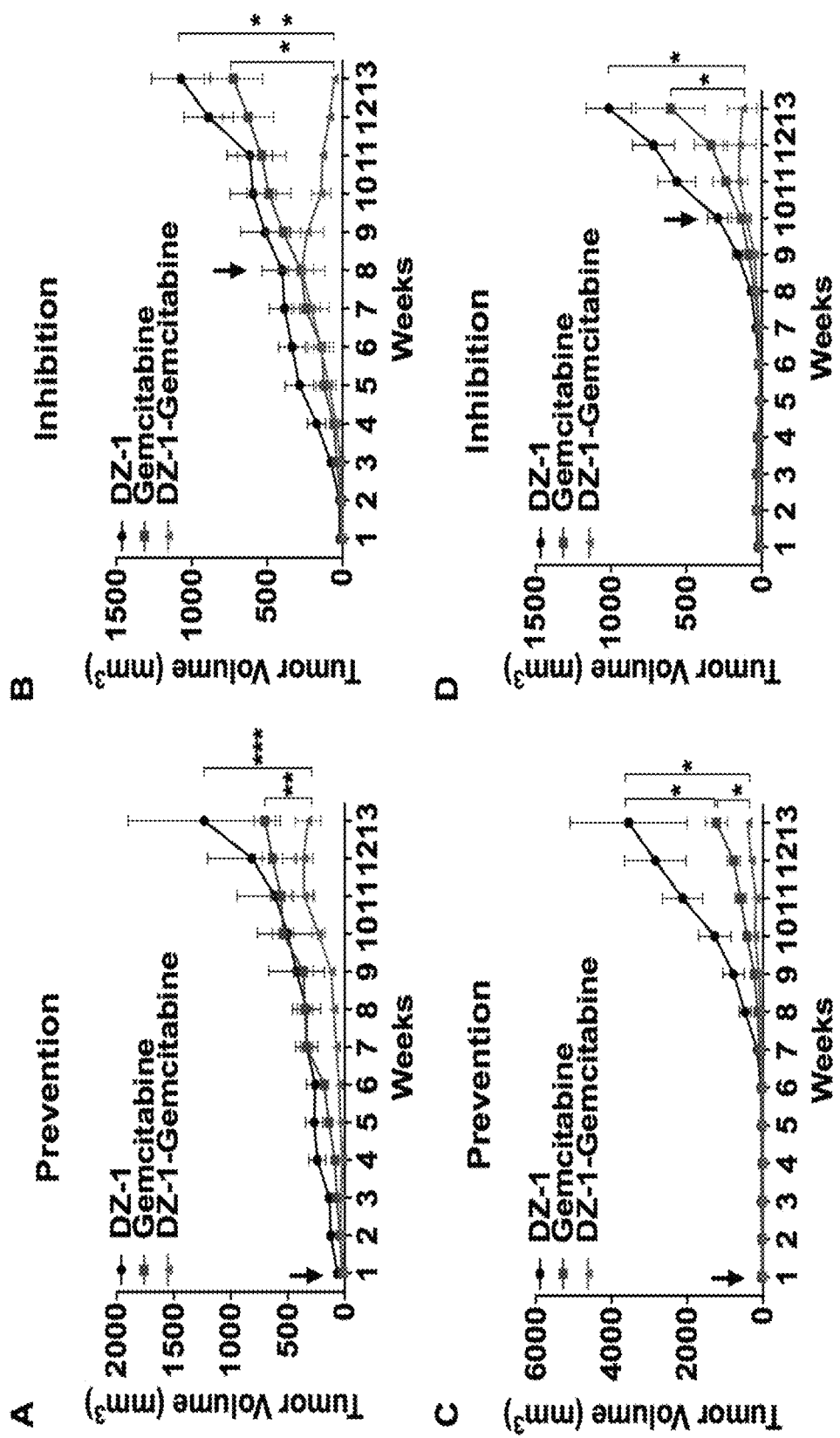
FIG. 6 shows effects of IR-783 (negative control), gemcitabine (positive control), and DZ-1-gemcitabine on prostate and pancreatic tumor growth in vivo by tumor volumes. (A) Prevention and (B) inhibition studies of subcutaneous tumor growth measured by tumor volumes of prostate cancer PC3 cells in mice treated with IR-783 (7.5 mg/kg; n=10), gemcitabine (2.5 mg/kg; n=10), and DZ-1-gemcitabine (10 mg/kg; n=10) twice a week via i.p. injection. (C) Prevention and (D) inhibition studies of subcutaneous tumor growth measured by tumor volume of pancreatic MIAPaCa cells in mice treated with IR-783 (7.5 mg/kg; n=10), Gemcitabine (2.5 mg/kg; n=10), and DZ-1-gemcitabine (10 mg/kg; n=10) twice a week via i.p. injection. Arrows indicate the onset of treatments. * p<0.05;  p<0.01; * p<0.001.

The effects of IR-783 (negative control), gemcitabine (positive control), and DZ-1-gemcitabine (DZ-1-Gem) on prostate and pancreatic tumor growth in vivo were investigated by tumor volumes. FIG. 6(A) shows prevention and FIG. 6(B) shows inhibition of subcutaneous tumor growth, as measured by tumor volumes of prostate cancer PC3 cells in mice treated with IR-783 (7.5 mg/kg; n=10), gemcitabine (2.5 mg/kg; n=10), and DZ-1-gemcitabine (10 mg/kg; n=10) twice a week via i.p. injections. FIG. 6(C) shows prevention and FIG. 6(D) shows inhibition of subcutaneous tumor growth, as measured by tumor volume of pancreatic MIAPaCa cells in mice treated with IR-783 (7.5 mg/kg; n=10), Gemcitabine (2.5 mg/kg; n=10), and DZ-1-gemcitabine (10 mg/kg; n=10) twice a week via i.p. injections. Arrows indicate the onset of treatments. * p<0.05;  p<0.01; * p<0.001.

As can be seen from the results in FIGS. 6(A)-6(D), DZ-1-GEM is more effective than Gemcitabine in both prevention and inhibition of tumor cell growths in these studies.

Figure 7:
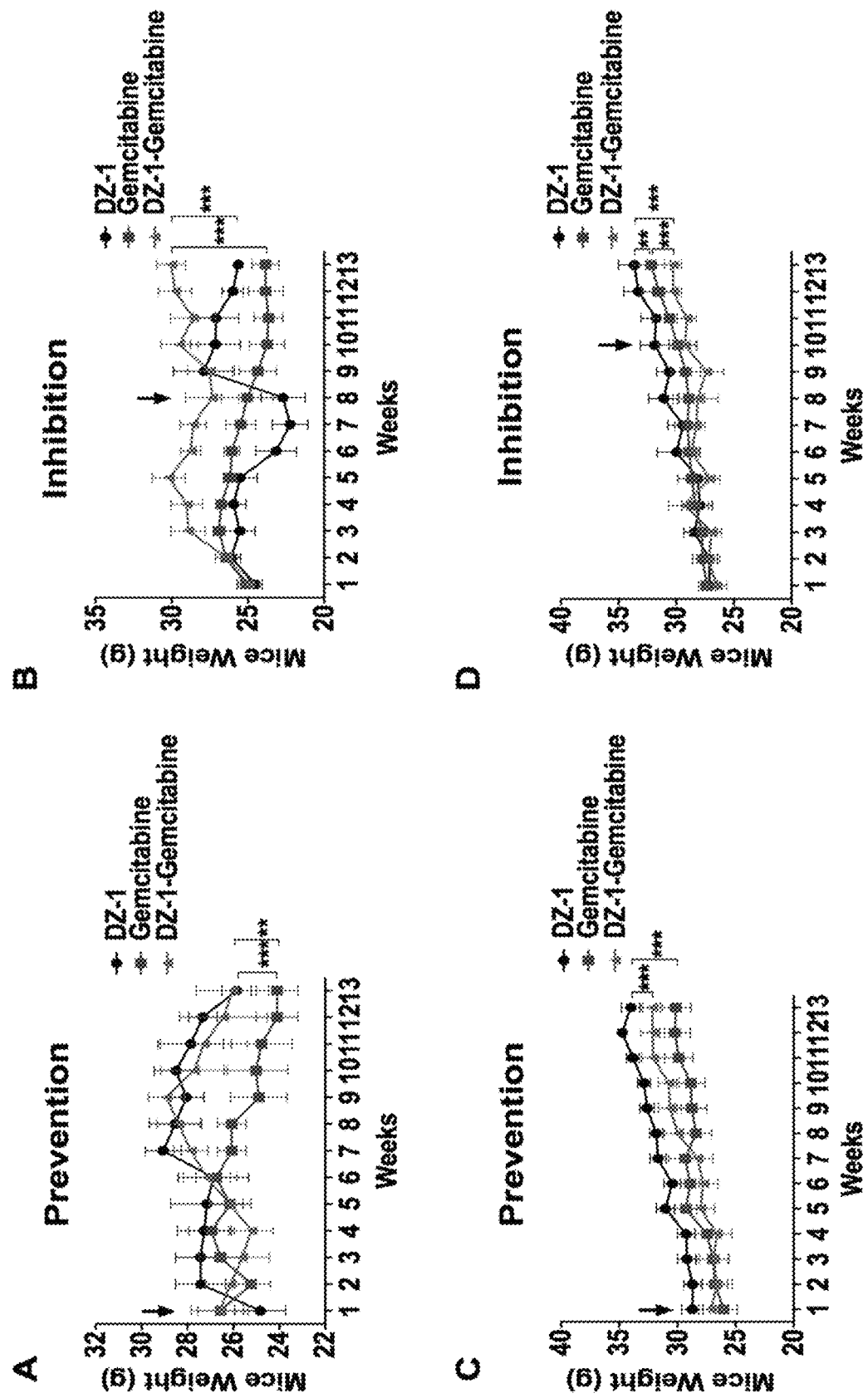
FIG. 7 shows effects of IR-783, Gemcitabine, and DZ-1-Gemcitabine on mice weight in mice bearing prostate and pancreatic tumors. Mice weights were measured in (A, C) prevention and (B, D) inhibition studies of subcutaneous PC3 and MIAPaCa tumors treated with IR-783 (7.5 mg/kg; n=10), Gemcitabine (2.5 mg/kg; n=10), and DZ-1-Gemcitabine (10 mg/kg; n=10) twice a week via i.p. injection. Arrows indicate the onset of treatments. * p<0.05;  p<0.01; * p<0.001.

The effects of IR-783, Gemcitabine, and DZ-1-Gemcitabine on mice weight in mice bearing prostate and pancreatic tumors were also investigated. Mice weights were measured in prevention (FIG. 7(A) and FIG. 7(C)) and inhibition (FIG. 7(B) and FIG. 7(D)) studies of subcutaneous PC3 and MIAPaCa tumors, treated with IR-783 (7.5 mg/kg; n=10), Gemcitabine (2.5 mg/kg; n=10), and DZ-1-Gemcitabine (10 mg/kg; n=10) twice a week via i.p. injections. Arrows indicate the onset of treatments. * $p<0.05$;  $p<0.01$; * $p<0.001$.

As can be seen from the results in FIGS. 7(A)-7(D), DZ-1-GEM has less impact on mouse body weights, as compared with Gemcitabine, in both prevention and inhibition studies.

Figure 8:
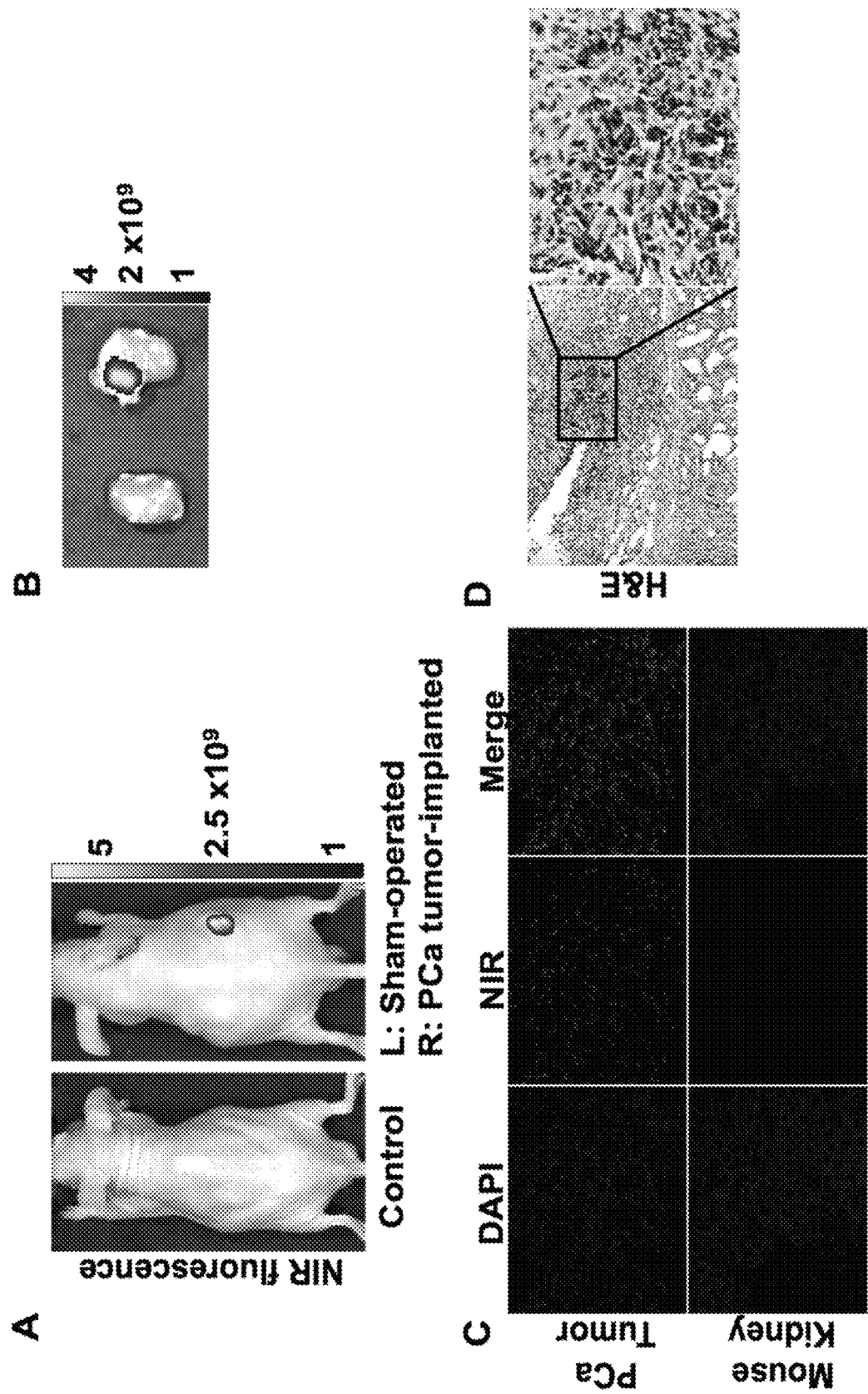
FIG. 8 shows uptake of NIR dye MHI-148 by prostate PDX tumors implanted in mouse subrenal capsules. (A) Representative NIR fluorescence imaging of control mouse with no tumor and mouse with sham-operation and PCa implantation in the subrenal capsules of the kidneys. Mice were injected i.p with NIR dye, MHI-148, 48 hours before fluorescence imaging at excitation of 783 nm and emission of 840 nm. Only the PCa tumor implanted in the subrenal capsule of the right kidney showed the NIR fluorescence signal but the sham-operated kidney of the left side nor the control mouse. (B) Representative ex vivo NIR fluorescence imaging of kidneys with sham operation and PCa tumor implantations. NIR fluorescence signal was only detected in the growing PCa tumors implanted in the subrenal capsule of the right kidney. (C) Fluorescent microscopy of DAPI, NIR, and merged images of frozen sections of the human PCa tumor and the mouse kidney from the subrenal xenograft model (200× magnification) (D) Representative H&E staining of the PCa tumors implanted in the mouse kidney capsule (40× magnification; inlet: 400× magnification).

The uptakes of NIR dye MHI-148 by prostate PDX tumors implanted in mouse subrenal capsules were investigated. FIG. 8(A) shows representative NIR fluorescence imaging of control mouse with no tumor and mouse with sham-operation and prostate cancer implantation in the subrenal capsules of the kidneys. Mice were injected i.p with NIR dye, MHI-148. After 48 hours, fluorescence imaging was performed with an excitation of 783 nm and emission of 840 nm. Only the prostate cancer tumor implanted in the subrenal capsule of the right kidney showed the NIR fluorescence signal, whereas the sham-operated kidney of the left side and the control mouse did not show any signal. FIG. 8(B) shows representative ex vivo NIR fluorescence imaging of kidneys with sham operation and prostate cancer tumor implantations. NIR fluorescence signal was only detected in the growing prostate cancer tumors implanted in the subrenal capsule of the right kidney. FIG. 8(C) shows fluorescent microscopy of DAPI, NIR, and merged images of frozen sections of the human prostate cancer tumor and the mouse kidney from the subrenal xenograft model (200× magnification). FIG. 8(D) shows representative H&E staining of the prostate cancer specimens implanted in the mouse kidney capsule (40× magnification; inlet: 400× magnification).

Figure 9:
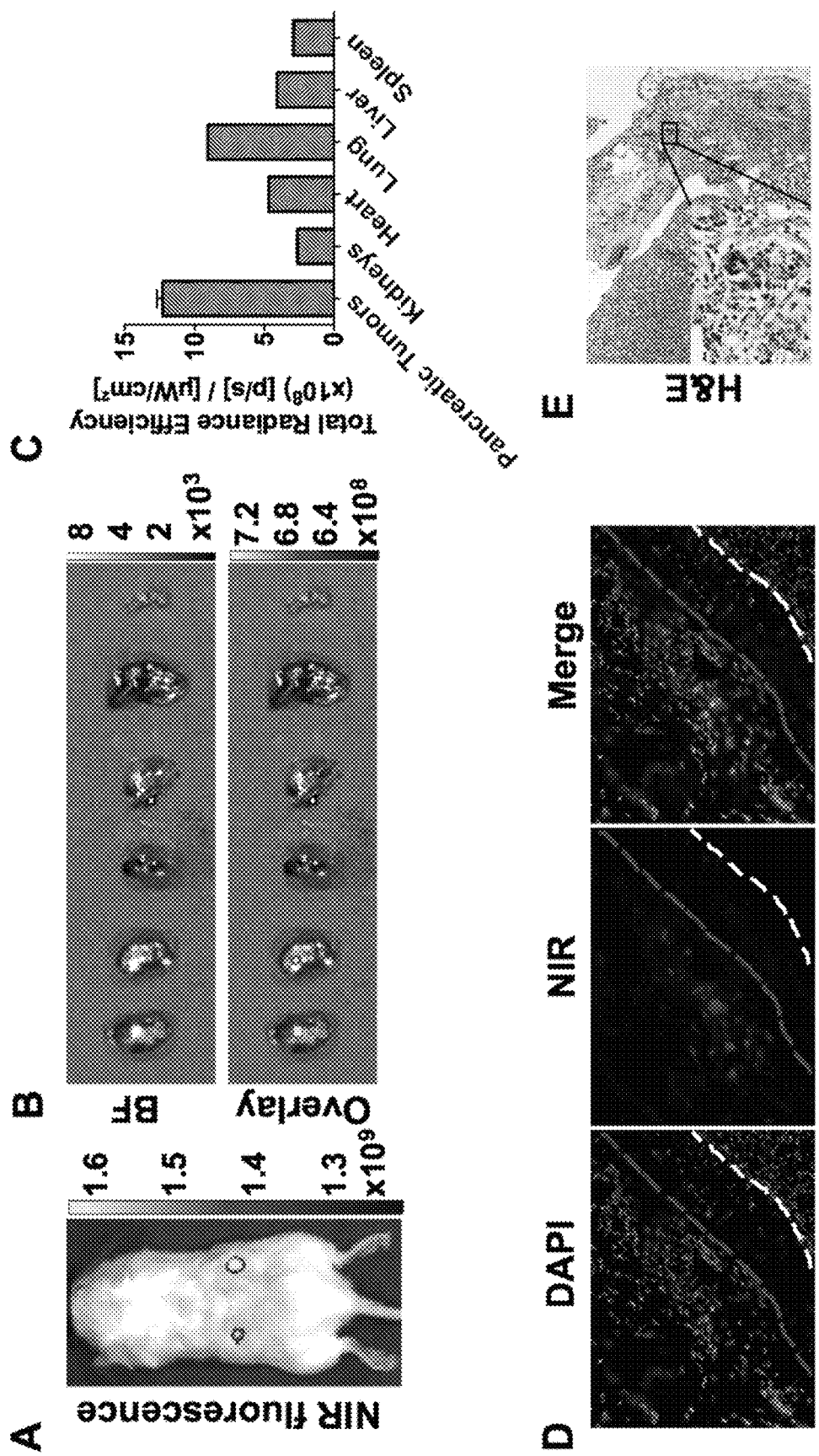
FIG. 9 shows uptake of NIR dye MHI-148, by pancreatic PDX tumors implanted in mouse subrenal capsules. (A) NIR fluorescent imaging of mouse bearing human pancreatic PDX tumors in subrenal capsules (excitation: 783 nm; excitation: 840 nm) (B) Ex vivo bright field and NIR fluorescent imaging of pancreatic PDX tumors in the kidney capsules and other organs harvested from mouse and (C) the NIR fluorescent intensity was quantified for the tumor and for each organ (total radiance efficiency [p/s]/[μW/cm²]) (D) Fluorescent microscopy of DAPI, NIR, and merged images of frozen section of pancreatic PDX tumor in the kidney capsule. White dash line outlines the mouse kidney and red dash line outlines the pancreatic PDX tumor. Only the pancreatic tumor uptakes the NIR dye but not by the mouse kidney (200× magnification) (E) H&E staining of the pancreatic PDX tumors in the mouse kidney capsule (40× magnification; inlet: 400× magnification).

The uptakes of NIR dye MHI-148, by pancreatic patient-derived xenografts (PDX) tumors implanted in mouse subrenal capsules were investigated. FIG. 9(A) shows NIR fluorescent imaging of mouse bearing human pancreatic PDX tumors in subrenal capsules (excitation: 783 nm; excitation: 840 nm). FIG. 9(B) shows ex vivo bright field and NIR fluorescent imaging of pancreatic PDX tumors in the kidney capsules and other organs harvested from mouse, and FIG. 9(C) shows the NIR fluorescent intensity was quantified for the tumor and for each organ (total radiance efficiency [p/s]/[μW/cm$^2$]). FIG. 9(D) shows fluorescent microscopy of DAPI, NIR, and merged images of frozen section of the pancreatic PDX tumor in the kidney capsule. White dash line outlines the mouse kidney and red dash line outlines the pancreatic PDX tumor. Only the pancreatic tumor uptakes the NIR dye, but the mouse kidney tumor does not (200× magnification). FIG. 9(D) shows H&E staining of the pancreatic PDX tumors in the mouse kidney capsule (40× magnification; inlet: 400× magnification).

Figure 10:
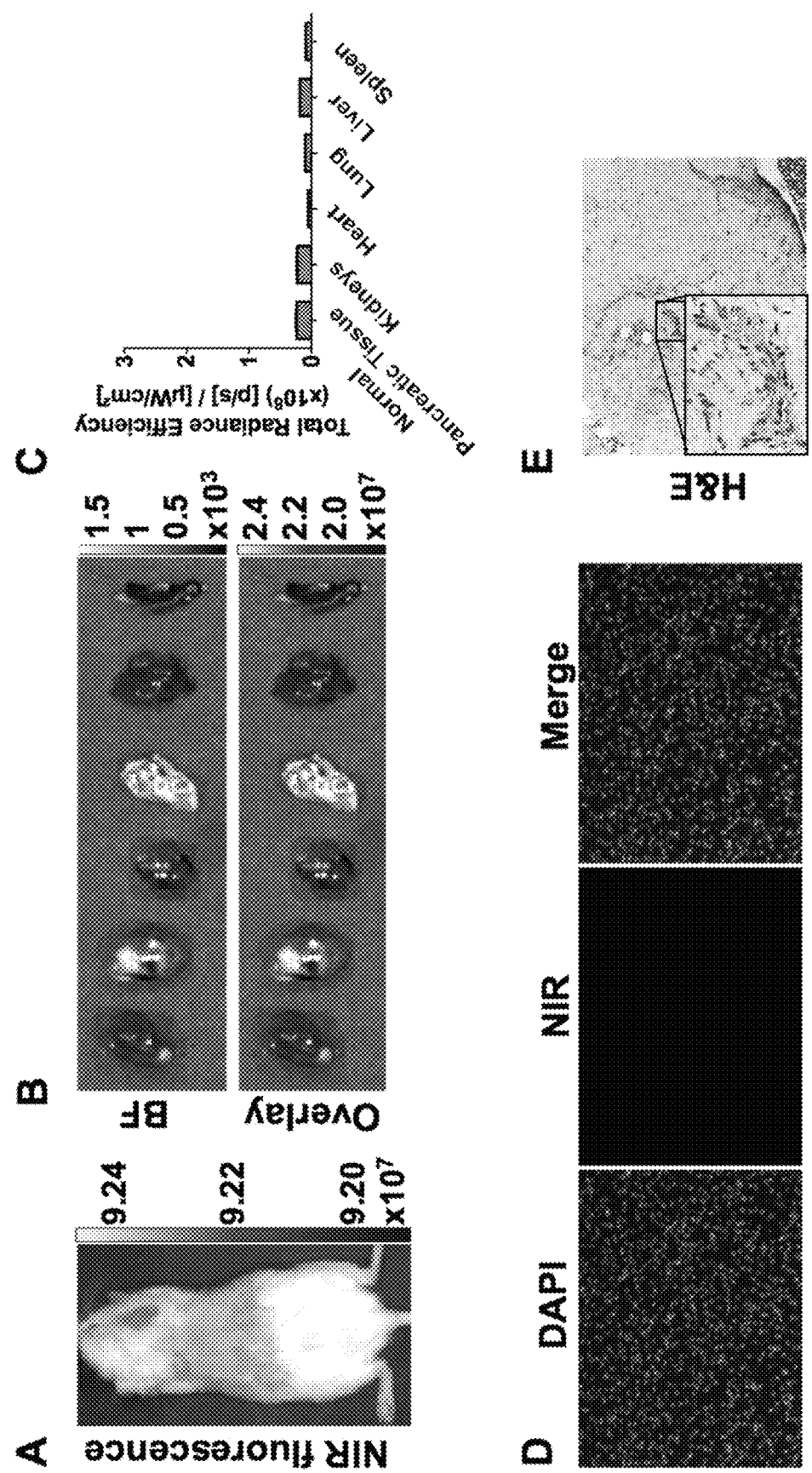
FIG. 10 shows uptake of NIR dye MHI-148 by normal pancreatic PDX tissue implanted in mouse subrenal capsules. (A) NIR fluorescent imaging of mouse bearing human pancreatic PDX tumors in subrenal capsules (excitation: 783 nm; excitation: 840 nm) (B) Ex vivo bright field and NIR fluorescent imaging of pancreatic PDX tumors in the kidney capsules and other organs harvested from mouse and (C) the NIR fluorescent intensity was quantified for the tumor and for each organ (total radiance efficiency [p/s]/[μW/cm²]) (D) Fluorescent microscopy of DAPI, NIR, and merged images of frozen section of pancreatic PDX tumor in the kidney capsule. White dash line outlines the mouse kidney and red dash line outlines the pancreatic PDX tumor. Only the pancreatic tumor uptakes the NIR dye but not by the mouse kidney (200× magnification) (E) H&E staining of the pancreatic PDX tumors in the mouse kidney capsule (40× magnification; inlet: 400× magnification).

The uptakes of NIR dye MHI-148 by normal pancreatic PDX tissue implanted in mouse subrenal capsules were investigated. FIG. 10(A) shows NIR fluorescent imaging of mouse bearing human pancreatic PDX tumors in subrenal capsules (excitation: 783 nm; excitation: 840 nm). FIG. 10(B) shows ex vivo bright field and NIR fluorescent imaging of pancreatic PDX tumors in the kidney capsules and other organs harvested from mouse, and FIG. 10(C) shows the NIR fluorescent intensity quantified for the tumor and for each organ (total radiance efficiency [p/s]/[μW/cm$^2$]). FIG. 10(D) shows fluorescent microscopy of DAPI. NIR, and merged images of frozen section of the pancreatic PDX tumor in the kidney capsule. White dash line outlines the mouse kidney and red dash line outlines the pancreatic PDX tumor. Only the pancreatic tumor uptakes the NIR dye, but the mouse kidney tumor does not (200× magnification). FIG. 10(D) shows H&E staining of the normal pancreatic PDX tissue in the mouse kidney capsule (40× magnification; inlet: 400× magnification).

Figure 11:
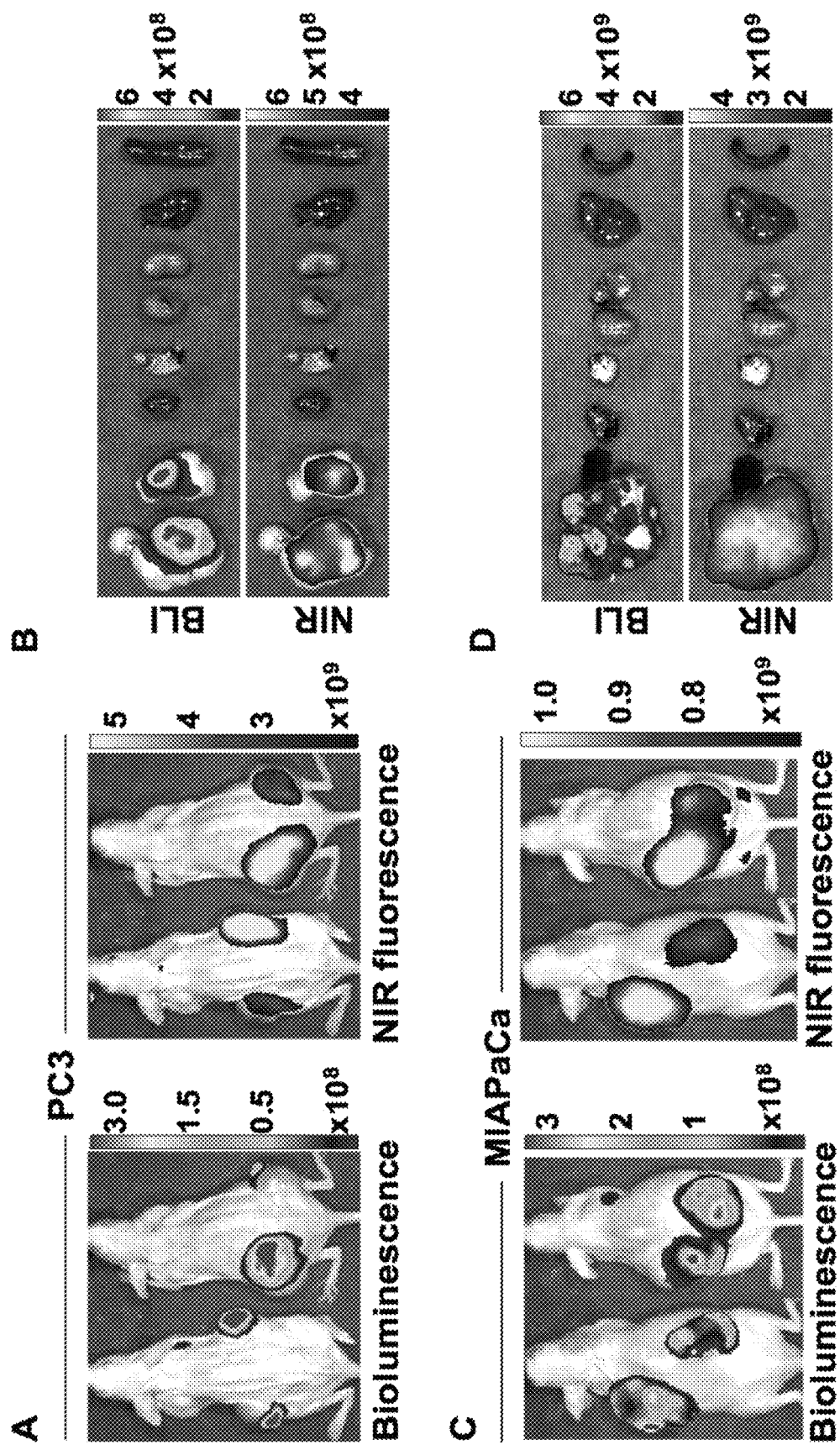
FIG. 11 shows uptake of DZ-1-gemcitabine specifically by prostate and pancreatic tumors but not normal organs in mice. (A) Representative bioluminescent and NIR fluorescent (excitation at 783 nm and emission at 840 nm) images of mice bearing subcutaneous luc-tagged PC3 tumors treated DZ-1-gemcitabine (10 mg/kg) (B) Representative ex vivo bioluminescent and NIR fluorescent imaging of the PC3 tumors and organs (heart, lung, kidneys, liver, and spleen) of the mice. (C) Representative bioluminescent and NIR fluorescent (excitation at 783 nm and emission at 840 nm) images of mice bearing subcutaneous luc-tagged MIAPaCa tumors treated DZ-1-gemcitabine (10 mg/kg) (D) Representative ex vivo bioluminescent and NIR fluorescent imaging of the MIAPaCa tumors and organs (heart, lung, kidneys, liver, and spleen) of the mice.

The uptakes of DZ-1-gemcitabine specifically by prostate and pancreatic tumors but not normal organs in mice were investigated. FIG. 11(A) shows representative bioluminescent and NIR fluorescent (excitation at 783 nm and emission at 840 nm) images of mice bearing subcutaneous luc-tagged PC3 tumors treated with DZ-1-gemcitabine (10 mg/kg). FIG. 11(B) shows representative ex vivo bioluminescent and NIR fluorescent imaging of the PC3 tumors and organs (heart, lung, kidneys, liver, and spleen) of the mice. FIG. 11(C) shows representative bioluminescent and NIR fluorescent (excitation at 783 nm and emission at 840 nm) images of mice bearing subcutaneous luc-tagged MIAPaCa tumors treated DZ-1-gemcitabine (10 mg/kg). FIG. 11(D) shows representative ex vivo bioluminescent and NIR fluorescent imaging of the MIAPaCa tumors and organs (heart, lung, kidneys, liver, and spleen) of the mice.

Figure 12:
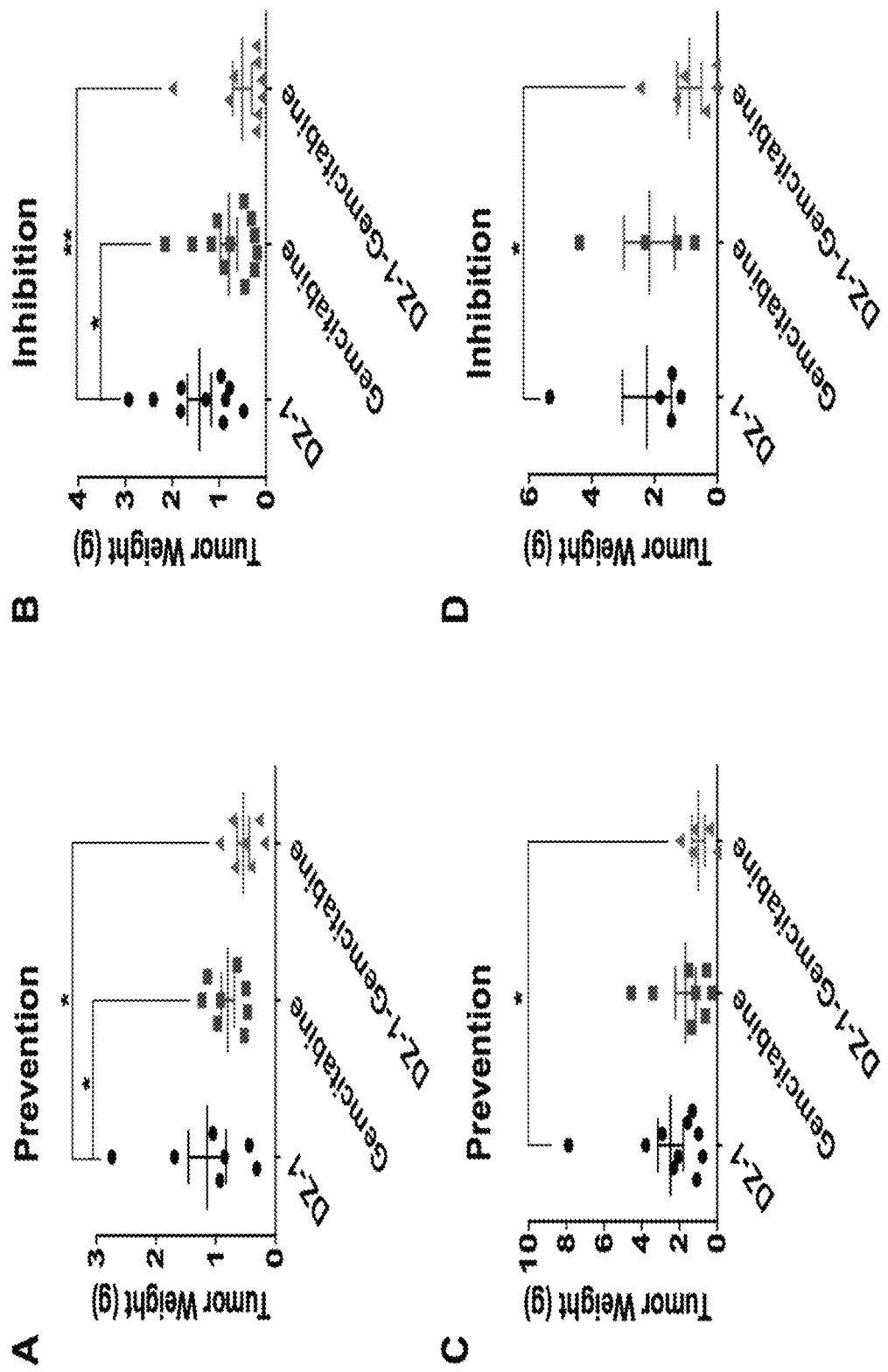
FIG. 12 shows effects of IR-783, Gemcitabine, and DZ-1-Gemcitabine on tumor weight in mice bearing prostate and pancreatic tumors. Tumor weights were measured in measured in (A,C) prevention and (B,D) inhibition studies of subcutaneous PC3 and MIAPaCa tumors treated with IR-783 (7.5 mg/kg; n=10), Gemcitabine (2.5 mg/kg; n=10), and DZ-1-Gemcitabine (10 mg/kg; n=10) twice a week via i.p. injection. Arrows indicate the onset of treatments. * $p<0.05$;  $p<0.01$; * $p<0.001$.

The effects of IR-783. Gemcitabine, and DZ-1-Gemcitabine on tumor weight in mice bearing prostate and pancreatic tumors were studied. Tumor weights were measured in measured in prevention (FIG. 12A and FIG. 12C) and inhibition (FIG. 12B and FIG. 12D) studies of subcutaneous PC3 and MIAPaCa tumors treated with IR-783 (7.5 mg/kg; n=10). Gemcitabine (2.5 mg/kg; n=10), and DZ-1-Gemcitabine (10 mg/kg; n=10) twice a week via i.p. injections. Arrows indicate the onset of treatments. * $p<0.05$;  $p<0.01$; * $p<0.001$.

Figure 13:
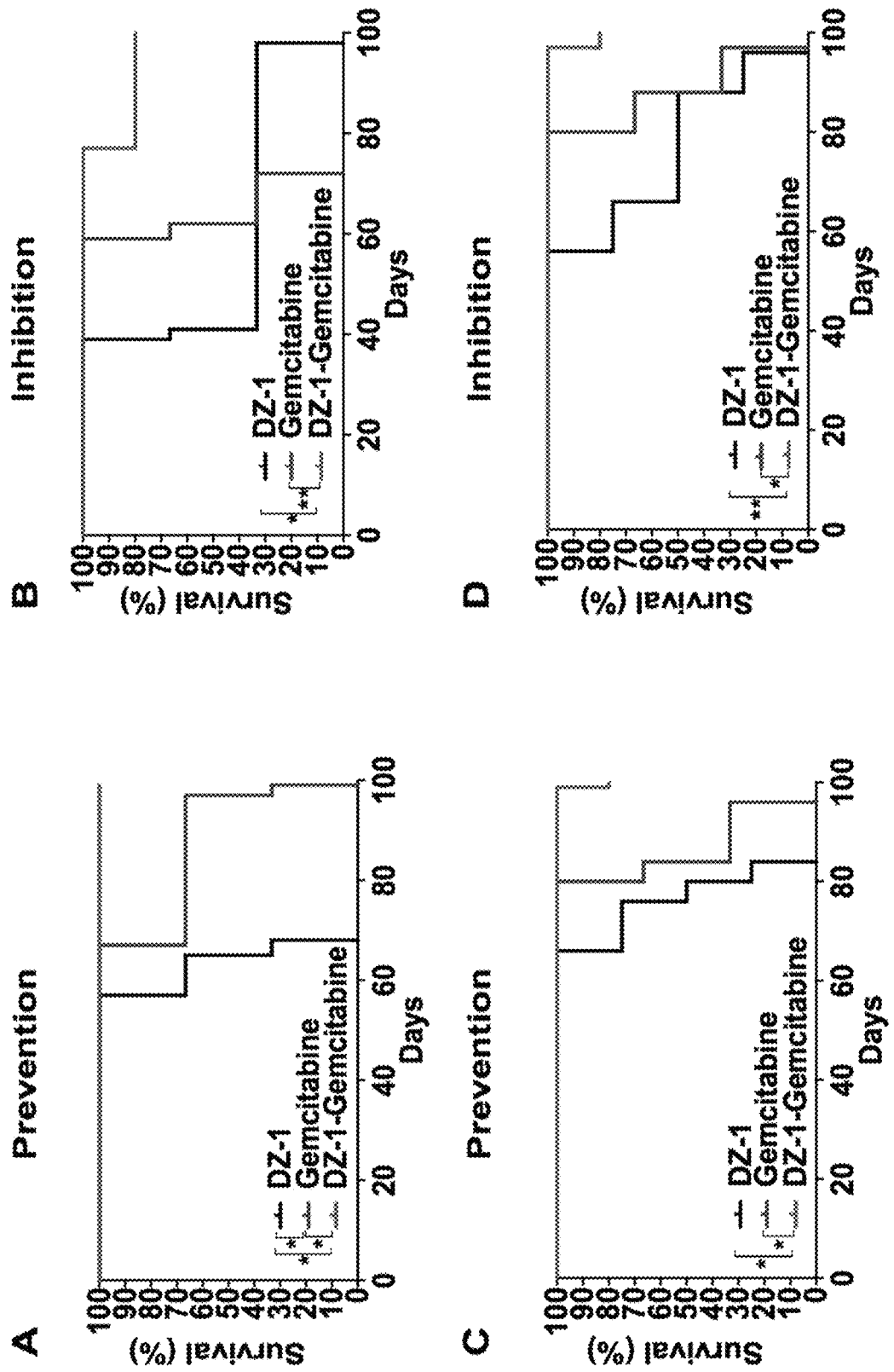
FIG. 13 shows effects of IR-783, Gemcitabine, and DZ-1-Gemcitabine on survival of mice bearing prostate PC3 and pancreatic MIAPaCa tumors. Kaplan-Meier survival curves of mice in each experimental group (n=5) in (A,C) prevention and (B,D) inhibition studies in prostate cancer and pancreatic cancer, respectively. * $p<0.05$;  $p<0.01$; * $p<0.001$.

The effects of IR-783. Gemcitabine, and DZ-1-Gemcitabine on survival of mice bearing prostate PC3 and pancreatic MIAPaCa tumors were studied. Kaplan-Meier survival curves of mice in each experimental group (n=5) in prevention (FIG. 13A and FIG. 13C) and inhibition (FIG. 13B and FIG. 13D) studies in prostate cancer and pancreatic cancer, respectively. * $p<0.05$;  $p<0.01$; * $p<0.001$.

Figure 14:
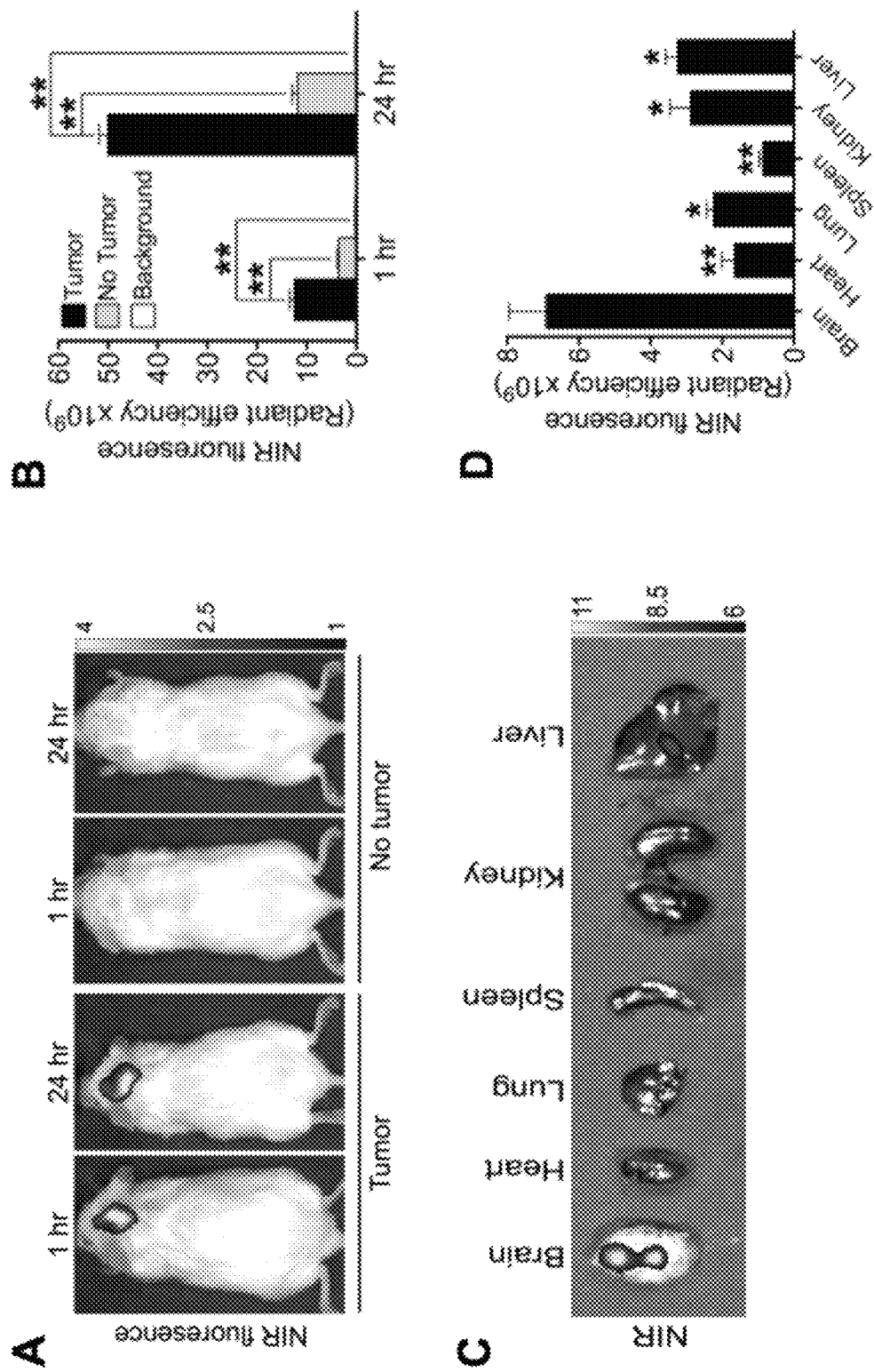
FIG. 14 shows uptake and retention of DZ-1-gemcitabine dye-drug conjugate (NIRG) in intracranial U87 tumor xenografts. (A) Uptake of NIRG (50 nmol/mouse, i.p.) by intracranial U87 tumor xenograft as determined by in vivo NIRF imaging at 1 h and 24 h time points after dye injection. Representative images are shown. (B) Quantitative analysis of uptake intensity in (A) (n ¼ 3, mean±SEM) **$p<0.01$. (C) Uptake and retention of NIRG by mouse brain and other indicated organs dissected from (B), as determined by ex vivo NIRF imaging 24 h after dye injection. (D) Quantitative analysis of organ-specific NIRF signal intensity in (D) (n ¼ 3, mean±SEM) *$p<0.05$, **$p<0.01$ as compared to brain.

The uptake and retention of DZ-1-gemcitabine dye-drug conjugate (NIRG) in intracranial U87 tumor xenografts were investigated. FIG. 14(A) shows uptake of NIRG (50 nmol/mouse, i.p.) by intracranial U87 tumor xenograft, as determined by in vivo NIRF imaging at 1 h and 24 h time points after dye injection. Representative images are shown. FIG. 14(B) shows the quantitative analysis of uptake intensities in FIG. 14(A) (n ¼ 3, mean±SEM) **$p<0.01$. FIG. 14(C) shows uptake and retention of NIRG by mouse brain and other indicated organs dissected from FIG. 14(B), as determined by ex vivo NIRF imaging 24 h after dye injection. FIG. 14(D) shows the quantitative analysis of organ-specific NIRF signal intensity in FIG. 14(D) (n ¼ 3, mean±SEM). *$p<0.05$, **$p<0.01$ as compared to brain.

Figure 15:
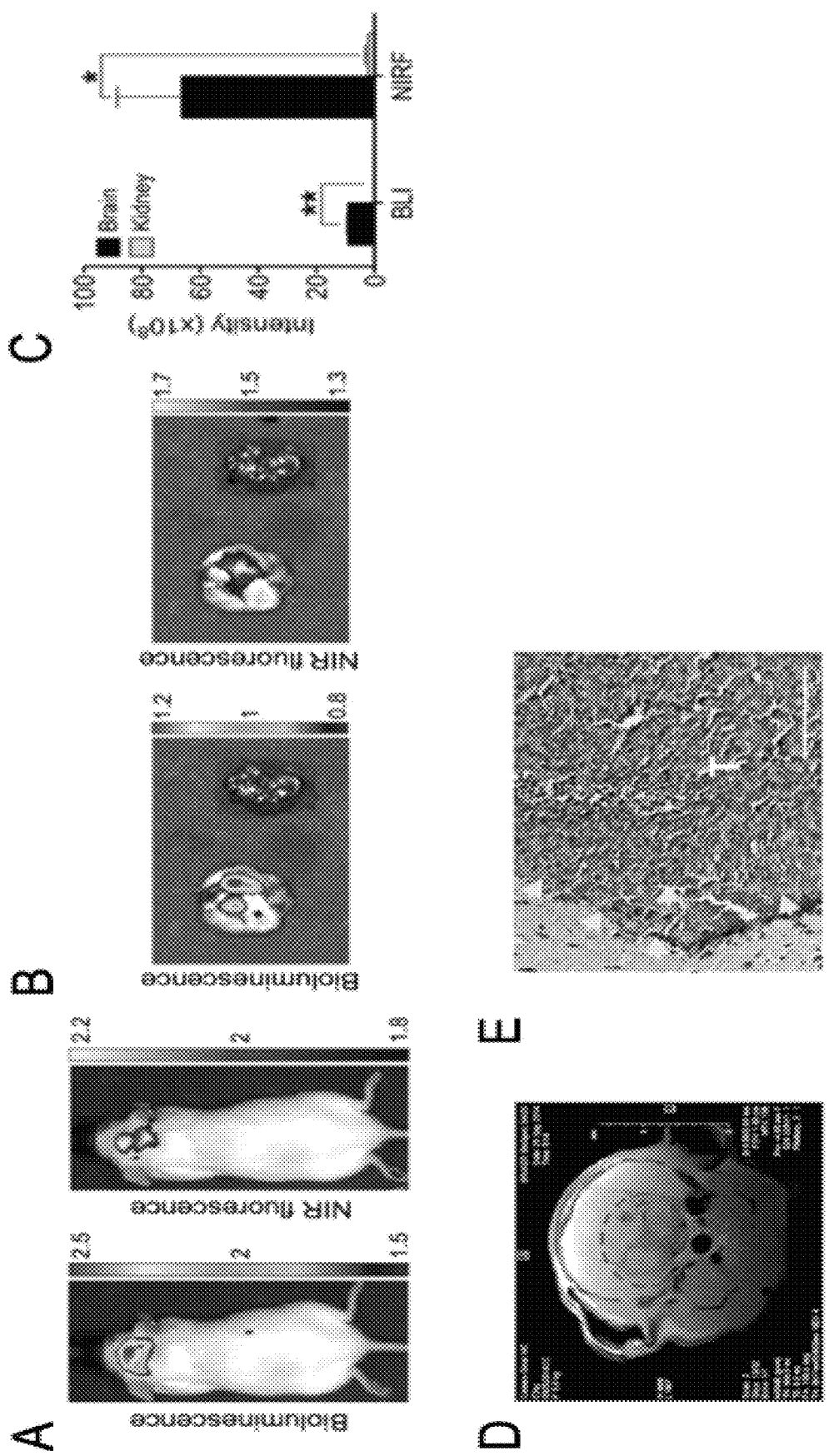
FIG. 15 shows uptake and retention of IR-783-gemcitabine dye-drug conjugate (NIRG) in xenograft prostate tumor brain metastases. (A, B) Mice bearing CW22Rv1 prostate tumor brain metastases were subjected to both BLI and NIRF imaging in vivo 24 h after NIRG (50 nmol/mouse, i.p.) (A) Mouse brain and control kidney were subsequently excised and subjected ex vivo to both imaging modalities (B) (C) Quantitative analysis of both BLI and NIRF signal intensity in (B) (n ¼ 3, mean±SEM) *$p<0.05$, **$p<0.01$. (D) MRI T2 scan of tumor-bearing mouse brain. Tumor area is indicated in red dashed circle. (E) H&E stain of prostate tumor brain metastases (T) Yellow arrows indicate invasive edges. Original magnification, 400; scale bar: 20 mm.

The uptake and retention of IR-783-gemcitabine dye-drug conjugate (NIRG) in xenograft prostate tumor brain metastases were investigated. FIG. 15A shows mice bearing CW22Rv1 prostate tumor brain metastases and having been subjected to both BLI and NIRF imaging in vivo 24 h after NIRG (50 nmol/mouse, i.p.). FIG. 15(B) shows mouse brain and control kidney were subsequently excised and subjected ex vivo to both imaging modalities. FIG. 15(C) shows the quantitative analysis of both BLI and NIRF signal intensity in FIG. 15(B) (n ¼ 3, mean±SEM) *p<0.05, **p<0.01. FIG. 15(D) shows MRI T2 scan of tumor-bearing mouse brain. Tumor area is indicated in red dashed circle. FIG. 15(E) shows H&E stain of prostate tumor brain metastases (T). Yellow arrows indicate invasive edges. Original magnification, 400; scale bar: 20 mm.

The above examples demonstrate various aspect and utility of embodiments of the invention. While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A dye-drug conjugate comprising the following structure:

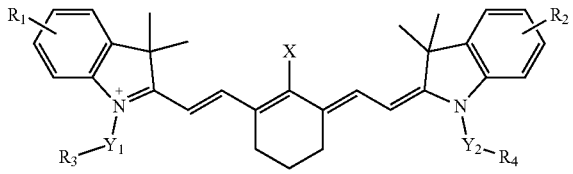

wherein $R_1$ and $R_2$ are independently selected from the group consisting of —H, alkyl, alkyl-sulphonate, alkylcarboxylic, alkylamino, aryl, —SO$_3$H, —PO$_3$H, —OH, —NH$_2$, and -halogen;

wherein $Y_1$ and $Y_2$ is independently selected from the group consisting of alkyl, aryl, aralkyl, alkylsulphonate, alkylcarboxylic, alkylamino, ω-alkylaminium, ω-alkynyl, PEGyl, PEGylcarboxylate, ω-PEGylaminium, ω-acyl-NH, ω-acyl-lysinyl-, ω-acyl-triazole, ω-PEGylcarboxyl-NH—, ω-PEGylcarboxyl-lysinyl, and ω-PEGylcarboxyl-triazole;

wherein X is selected from the group consisting of a hydrogen, halogen, CN, Me, NH$_2$, SH and OH; and $R_3$ is gemcitabine and $R_4$ is a therapeutic agent or an imaging moiety, wherein the therapeutic agent is selected from the group consisting of a platinum-based therapeutic agent, a small molecule therapeutic agent, a peptide, a protein, a polymer, an siRNA, a microRNA, and a nanoparticle, wherein the imaging moiety is a small molecule labeled with a radio-isotope selected from the group consisting of F18, I-125, I-124, I-123, I-131, or wherein the therapeutic agent and/or the imaging moiety is a chelator-complexed radioactive isotope, wherein the radioactive isotope is selected from the group consisting of Cu-64, In-111, Tc-99m, Ga-68, Lu-177, Zo-89, Th-227, and Gd-157.

2. The dye-drug conjugate according to claim 1, wherein X is a halogen.

3. The dye-drug conjugate according to claim 2, wherein X is chloro.

4. The dye-drug conjugate according to claim 1, wherein $R_4$ comprises an imaging moiety.

5. The dye-drug conjugate according to claim 1, wherein $R_4$ comprises a therapeutic agent.

6. A dye-drug conjugate selected from the group consisting of:

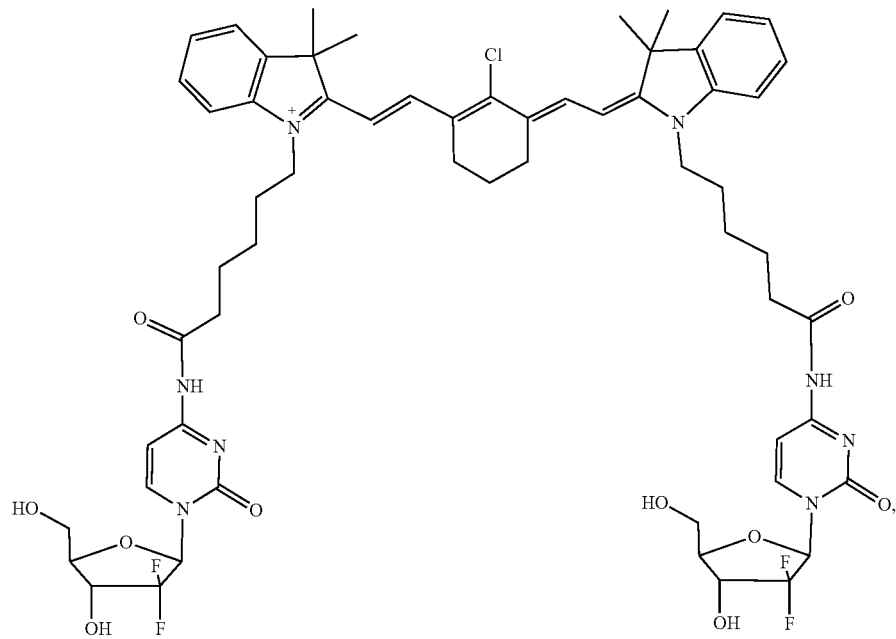

DZ-4

-continued
DZ-5
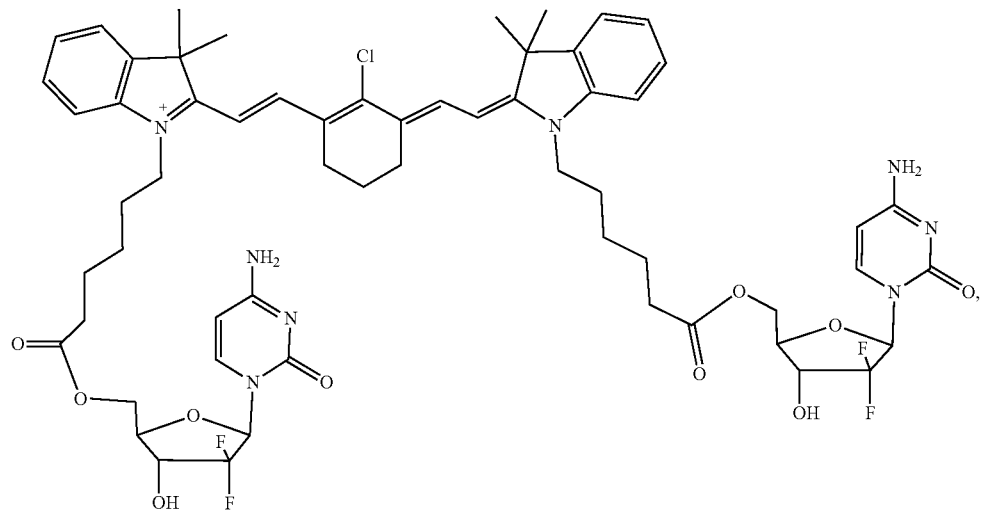
DZ-8
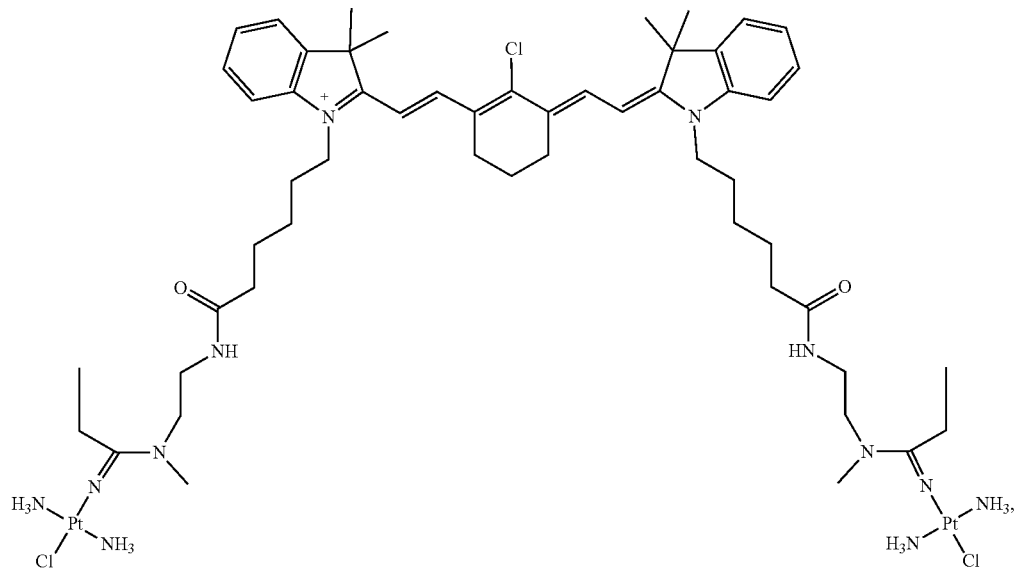
DZ-9
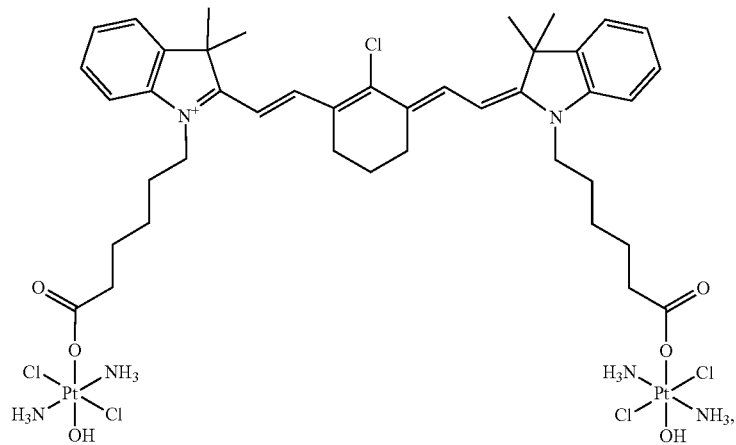

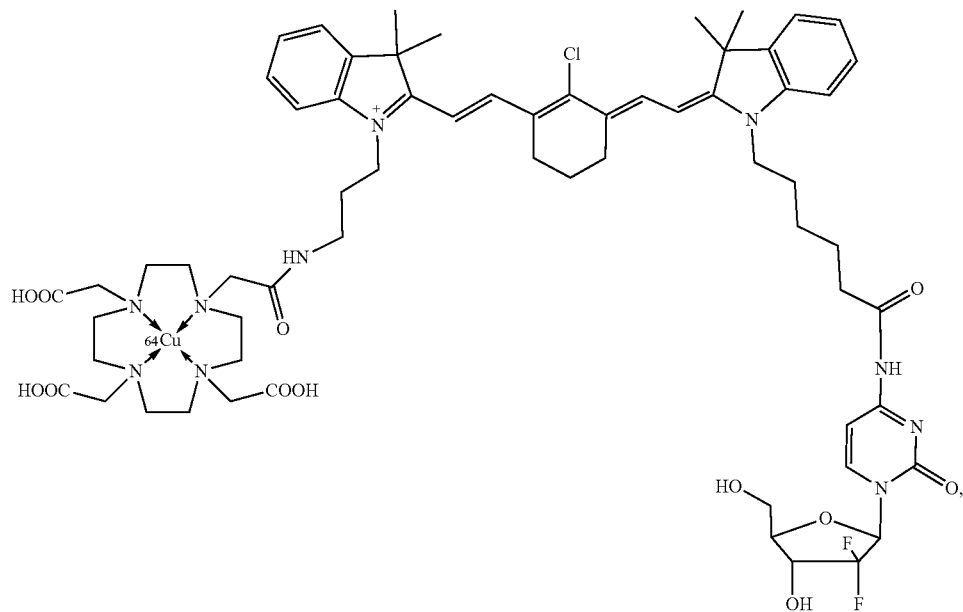
DZ-10
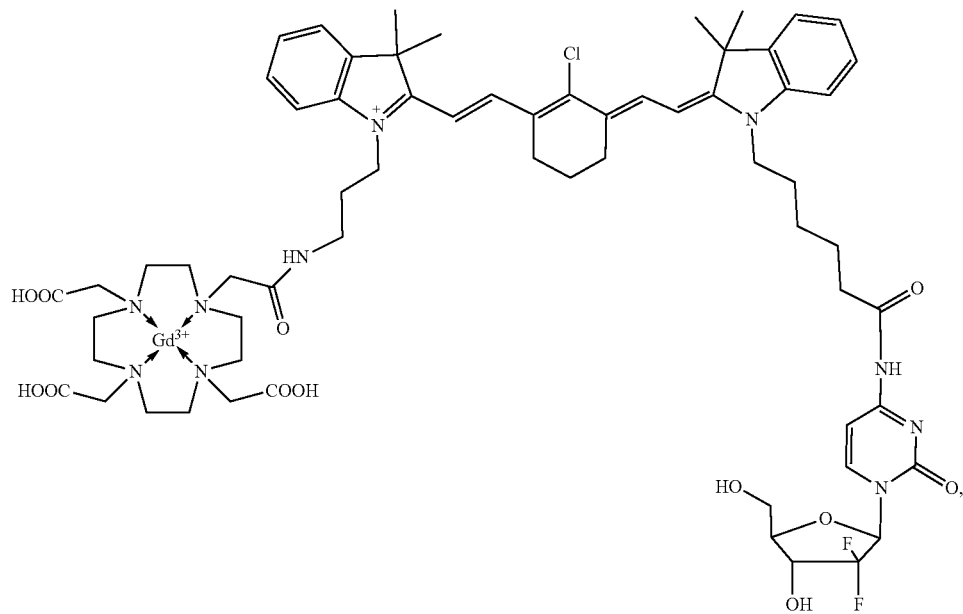
DZ-11

-continued

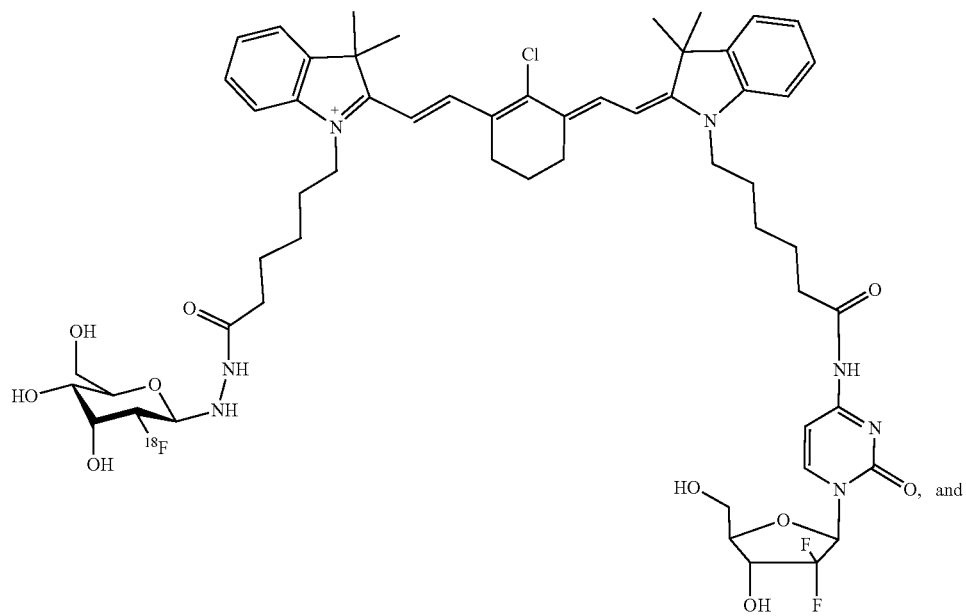

DZ-12

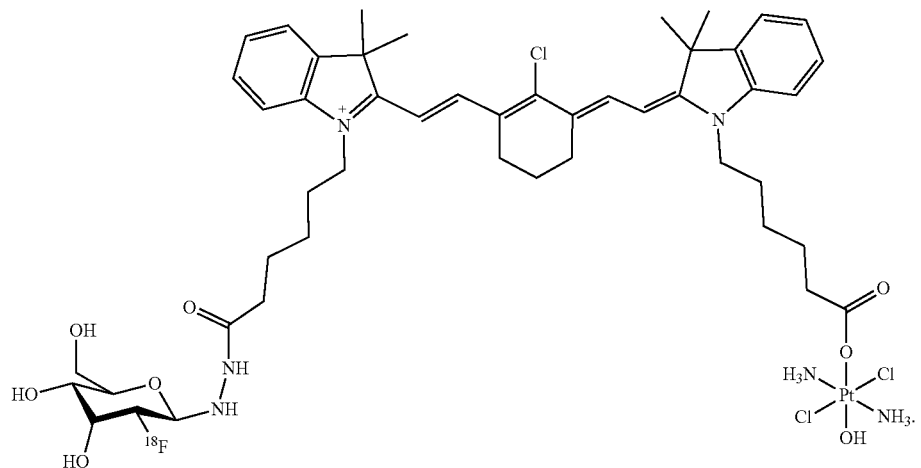

DZ-13

7. A method for diagnosing, detecting, or treating cancer, comprising the steps of administering to a subject having or suspected of having cancer the dye-drug conjugate according to claim 1 and optionally imaging the subject.

8. The method according to claim 7, wherein the cancer is one selected from the group consisting of prostate cancer, breast cancer, renal cancer, pancreatic cancer, lung cancer, and hepatic cancer.

9. The dye-drug conjugate according to claim 2, wherein $R_4$ comprises an imaging moiety.

10. The dye-drug conjugate according to claim 3, wherein $R_4$ comprises an imaging moiety.

11. The dye-drug conjugate according to claim 2, wherein $R_4$ comprises a therapeutic agent.

12. The dye-drug conjugate according to claim 3, wherein $R_4$ comprises a therapeutic agent.

13. The method according to claim 7, wherein X is halogen.

14. The method according to claim 7, wherein X is chloro.

15. The method according to claim 7, wherein the dye-drug conjugate is one selected from the group consisting of:

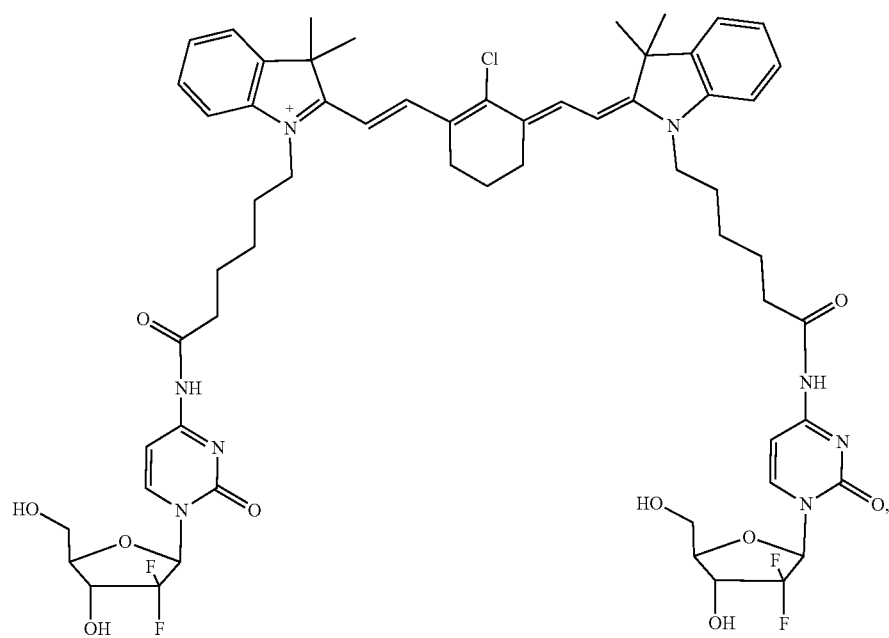
DZ-4
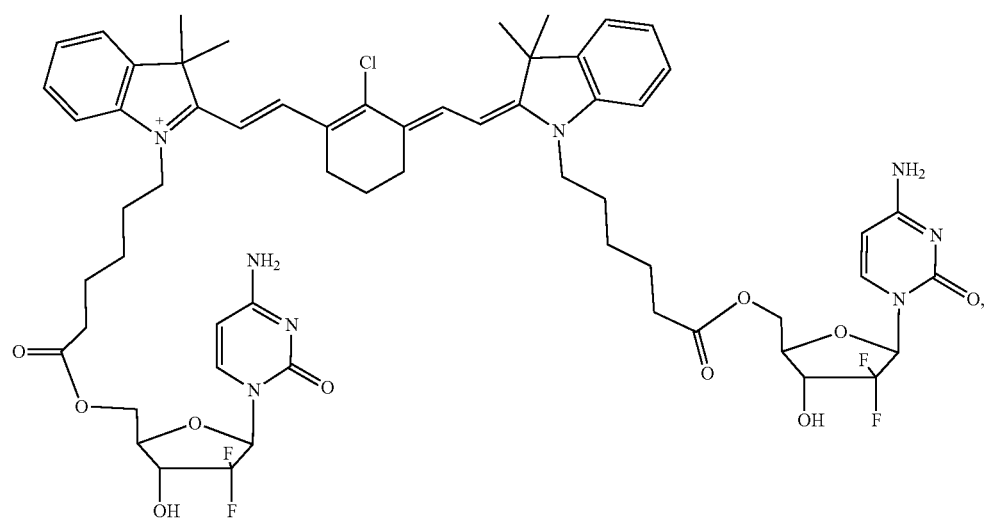
DZ-5

DZ-10
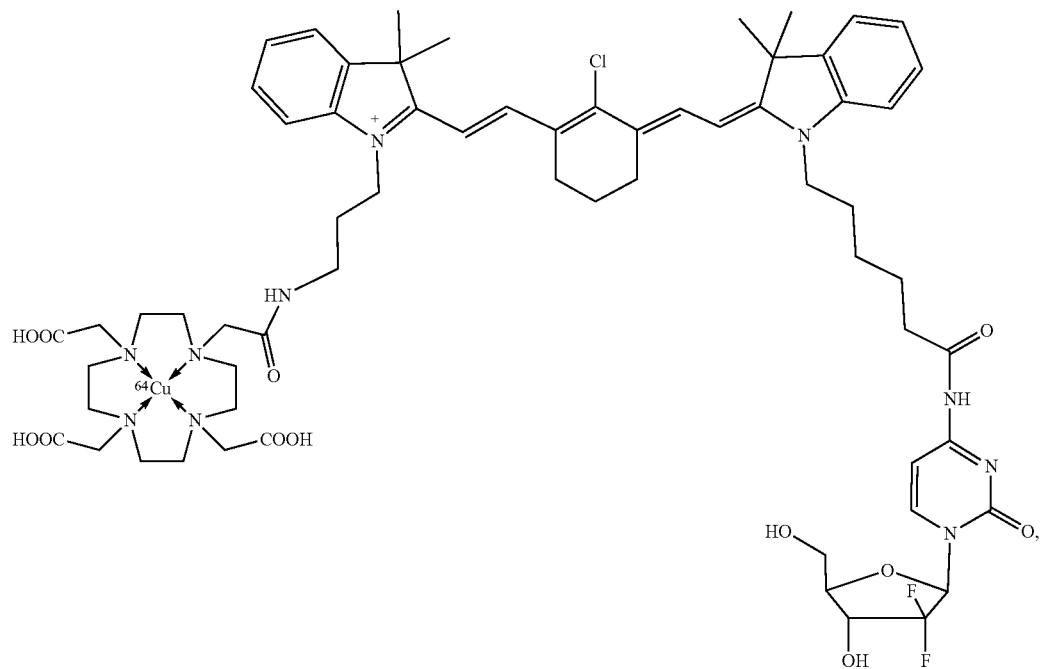
DZ-11
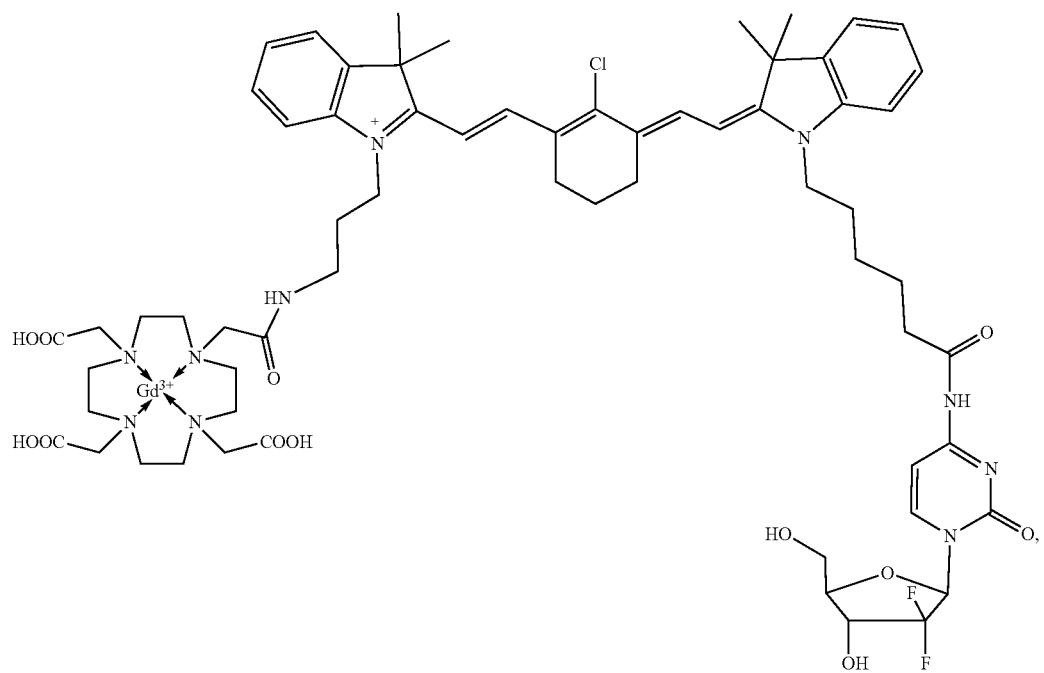

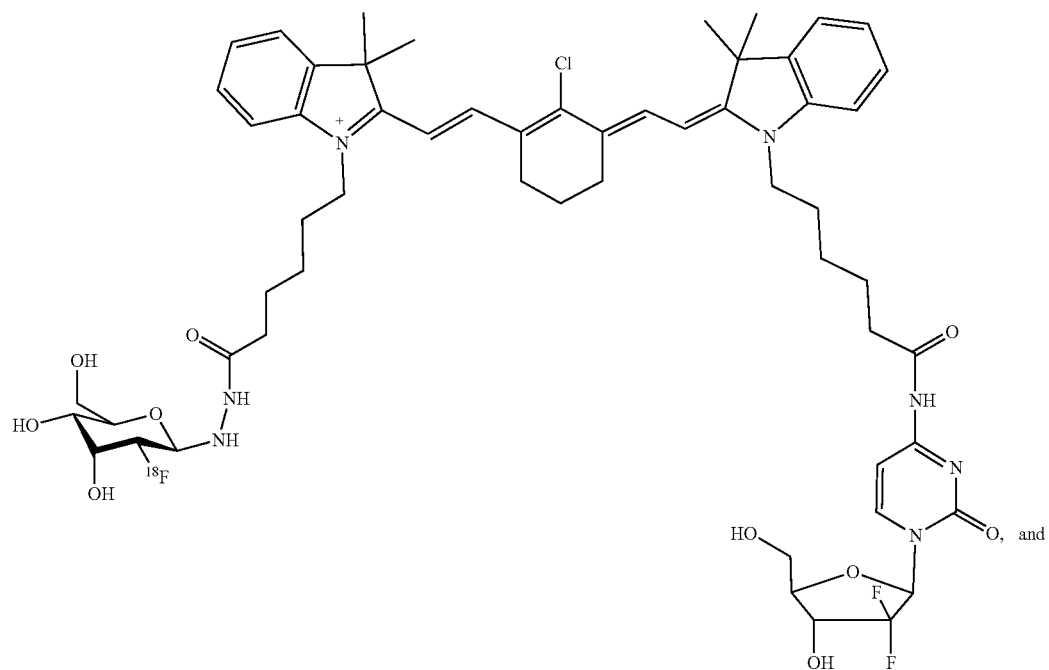
DZ-12
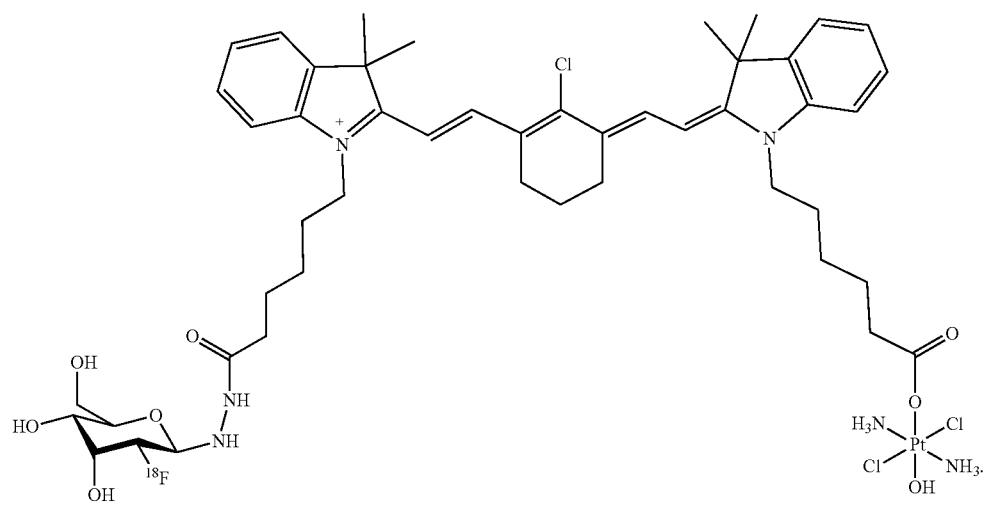
DZ-13
16. The method of claim 7, wherein $R_4$ comprises an imaging moiety.
17. The method of claim 7, wherein $R_4$ comprises a therapeutic agent.
18. A method for diagnosing, detecting, or treating cancer, comprising the steps of administering to a subject having or suspected of having cancer a dye-drug conjugate, wherein the dye-drug conjugate is selected from:

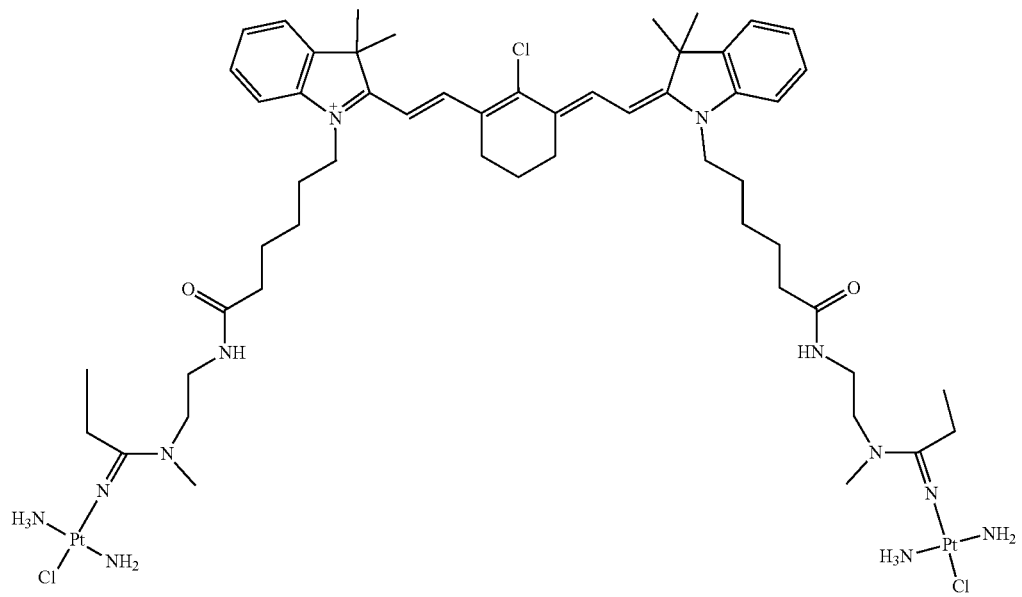
DZ-8
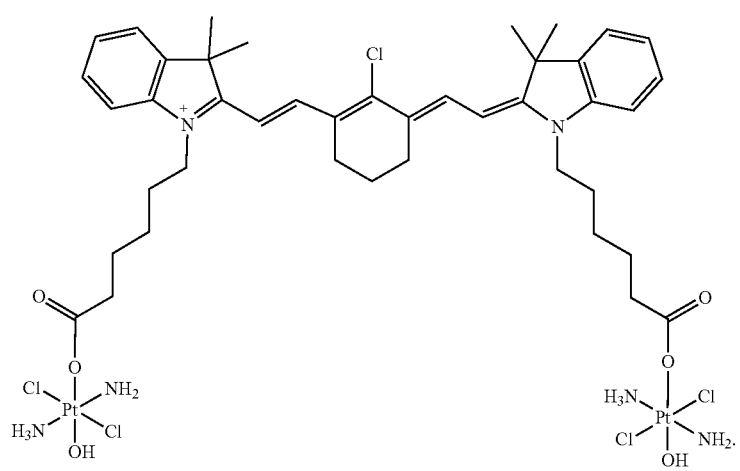
or
DZ-9
* * * * *